United States Patent
Pedros et al.

(10) Patent No.: US 11,266,472 B2
(45) Date of Patent: *Mar. 8, 2022

(54) ROBOTIC SURGICAL SYSTEMS AND INSTRUMENT DRIVE ASSEMBLIES

(71) Applicant: Covidien LP, Mansfield, MA (US)

(72) Inventors: Robert Pedros, Oxford, CT (US);
Brian Rockrohr, Guilford, CT (US);
Michael Zemlok, Prospect, CT (US)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/988,895

(22) Filed: Aug. 10, 2020

(65) Prior Publication Data
US 2020/0367983 A1 Nov. 26, 2020

Related U.S. Application Data

(63) Continuation of application No. 16/065,924, filed as application No. PCT/US2016/067469 on Dec. 19, 2016, now Pat. No. 10,779,900.

(Continued)

(51) Int. Cl.
*A61B 17/28* (2006.01)
*F16H 25/18* (2006.01)
(Continued)

(52) U.S. Cl.
CPC .............. *A61B 34/35* (2016.02); *A61B 17/29* (2013.01); *A61B 17/295* (2013.01); *A61B 34/30* (2016.02);
(Continued)

(58) Field of Classification Search
CPC . A61B 17/00234; A61B 17/29; A61B 17/295; A61B 2017/00199;
(Continued)

(56) References Cited

U.S. PATENT DOCUMENTS

| 5,649,956 A | 7/1997 | Jensen et al. |
|---|---|---|
| 5,842,993 A | 12/1998 | Eichelberger et al. |

(Continued)

FOREIGN PATENT DOCUMENTS

| CN | 104363854 A | 2/2015 |
|---|---|---|
| WO | 2013075204 A1 | 5/2013 |

(Continued)

OTHER PUBLICATIONS

Chinese First Office Action dated Aug. 21, 2020 corresponding to counterpart Patent Application CN 201680076436.

(Continued)

*Primary Examiner* — Adam D Rogers

(57) ABSTRACT

An instrument drive assembly includes a housing assembly and a coupling assembly. The housing assembly includes a drive assembly. The coupling assembly releasably couples an instrument drive shaft to a drive member of the drive assembly and an instrument sleeve of the surgical instrument to the housing assembly. Actuation of a retention mechanism of the coupling assembly between a locked and unlocked configuration couples and decouples the instrument sleeve of the surgical instrument therewith.

21 Claims, 21 Drawing Sheets

Related U.S. Application Data

(60) Provisional application No. 62/272,250, filed on Dec. 29, 2015.

(51) Int. Cl.

| | | |
|---|---|---|
| *A61B 34/35* | (2016.01) | |
| *A61B 34/30* | (2016.01) | |
| *A61B 17/29* | (2006.01) | |
| *A61B 17/295* | (2006.01) | |
| *F16H 25/20* | (2006.01) | |
| *A61B 17/00* | (2006.01) | |

(52) U.S. Cl.
CPC ............. *F16H 25/18* (2013.01); *F16H 25/20* (2013.01); *A61B 2017/00367* (2013.01); *A61B 2017/00398* (2013.01); *A61B 2017/00477* (2013.01); *A61B 2017/2946* (2013.01); *F16H 2025/2071* (2013.01)

(58) Field of Classification Search
CPC .......... A61B 2017/00367; A61B 2017/00398; A61B 2017/00477; A61B 2017/2946; A61B 34/30; A61B 34/35; A61B 34/71; A61B 2034/715; F16H 25/18; F16H 25/20; F16H 25/2015; F16H 2025/2031; F16H 2025/204; F16H 2025/2071; F16H 2025/2075; F16H 2034/305; F16C 1/12; F16C 11/06
See application file for complete search history.

(56) References Cited

U.S. PATENT DOCUMENTS

| | | | |
|---|---|---|---|
| 6,758,843 | B2 | 7/2004 | Jensen |
| 8,343,141 | B2 | 1/2013 | Madhani et al. |
| 8,518,065 | B2 | 8/2013 | Shores |
| 8,636,192 | B2 | 1/2014 | Farascioni et al. |
| 8,828,023 | B2 | 9/2014 | Neff et al. |
| 8,925,786 | B2 | 1/2015 | Holsten et al. |
| 8,968,312 | B2 | 3/2015 | Marczyk et al. |
| 9,743,995 | B2 * | 8/2017 | Lohmeier ............ B25J 19/0075 |
| 10,085,750 | B2 | 10/2018 | Zergiebel et al. |
| 10,420,620 | B2 | 9/2019 | Rockrohr |
| 10,779,900 | B2 | 9/2020 | Pedros et al. |
| 2003/0083673 | A1 | 5/2003 | Tierney et al. |
| 2004/0049205 | A1 | 3/2004 | Lee et al. |
| 2005/0234435 | A1 | 10/2005 | Layer |
| 2007/0239172 | A1 | 10/2007 | Lee et al. |
| 2009/0024142 | A1 | 1/2009 | Ruiz Morales |
| 2010/0175701 | A1 | 7/2010 | Reis et al. |
| 2011/0118754 | A1 | 5/2011 | Dachs, II et al. |
| 2011/0174099 | A1 | 7/2011 | Ross et al. |
| 2011/0213362 | A1 | 9/2011 | Cunningham et al. |
| 2011/0213383 | A1 | 9/2011 | Lee et al. |
| 2012/0116416 | A1 | 5/2012 | Neff et al. |
| 2013/0123783 | A1 | 5/2013 | Marczyk et al. |
| 2013/0172713 | A1 | 7/2013 | Kirschenman |
| 2013/0331858 | A1 | 12/2013 | Devengenzo et al. |
| 2014/0012237 | A1 | 1/2014 | Pribanic et al. |
| 2014/0039387 | A1 | 2/2014 | Kim et al. |
| 2014/0163581 | A1 | 6/2014 | Devengenzo et al. |
| 2014/0276761 | A1 | 9/2014 | Parihar et al. |
| 2015/0105799 | A1 | 4/2015 | Lohmeier et al. |
| 2016/0199138 | A1 | 7/2016 | Cooper et al. |
| 2019/0099227 | A1 | 4/2019 | Rockrohr |
| 2020/0000538 | A1 | 1/2020 | Rockrohr |
| 2020/0237453 | A1 * | 7/2020 | Anglese ................ A61B 90/03 |
| 2020/0337787 | A1 * | 10/2020 | Anglese ............... A61B 17/295 |
| 2020/0337788 | A1 * | 10/2020 | Seow ..................... A61B 17/29 |
| 2021/0059709 | A1 * | 3/2021 | Black ............. A61B 17/320092 |
| 2021/0169457 | A1 * | 6/2021 | Traina ..................... A61B 34/30 |
| 2021/0220000 | A1 * | 7/2021 | Heiliger ................ A61B 17/29 |
| 2021/0220001 | A1 * | 7/2021 | Heiliger ................ A61B 34/37 |

FOREIGN PATENT DOCUMENTS

| | | |
|---|---|---|
| WO | 2016043845 A1 | 3/2016 |
| WO | 2016144998 A1 | 9/2016 |
| WO | 2019135940 A1 | 7/2019 |
| WO | 2019191015 A1 | 10/2019 |

OTHER PUBLICATIONS

Chinese Second Office Action dated Mar. 3, 2021 corresponding to counterpart Patent Application CN 201680076436.6.

Extended European Search Report dated Aug. 2, 2019 corresponding to counterpart Patent Application EP 16882352.4.

* cited by examiner

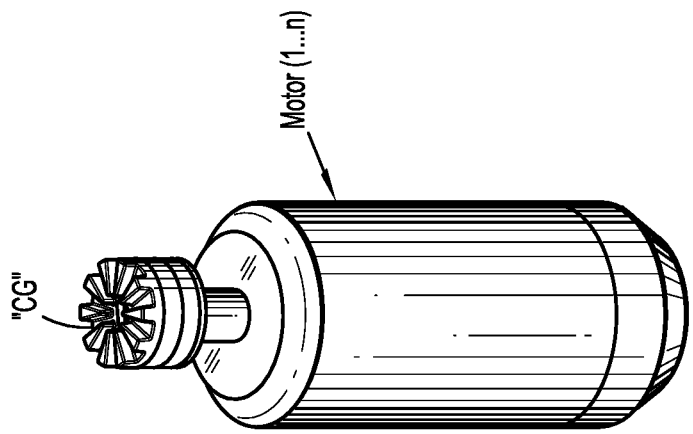
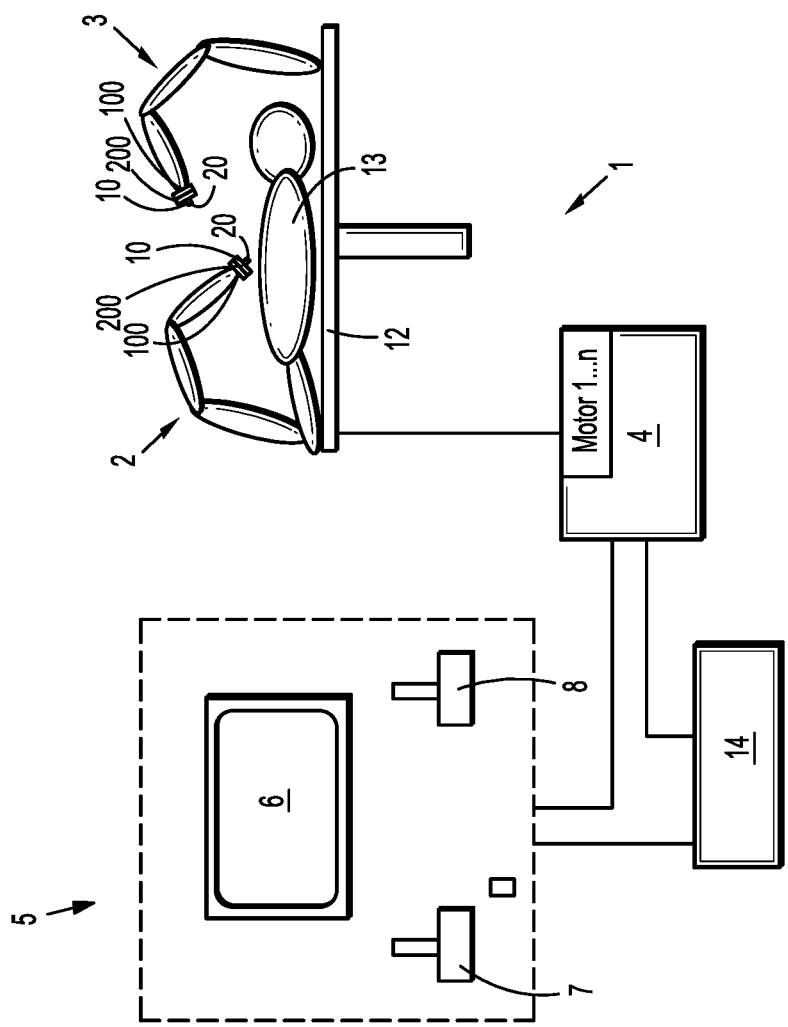
FIG. 1B
FIG. 1A

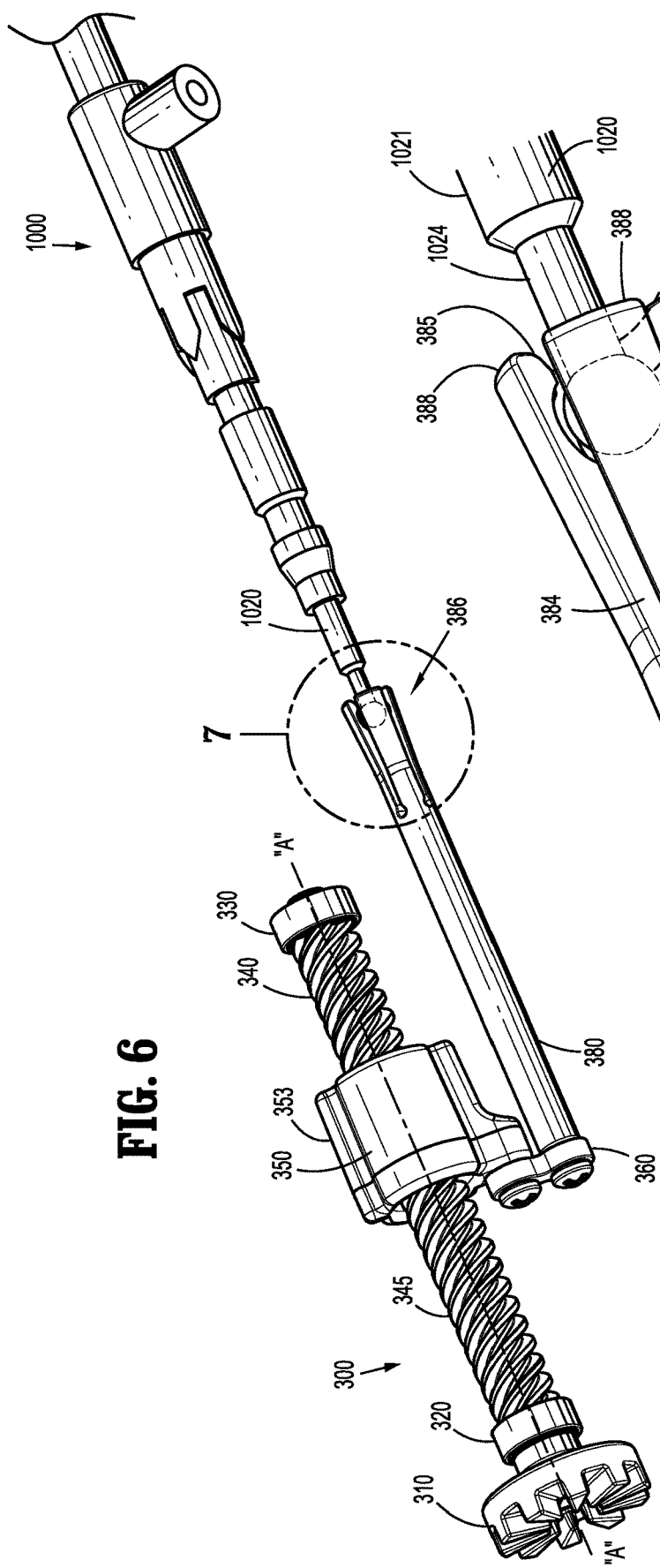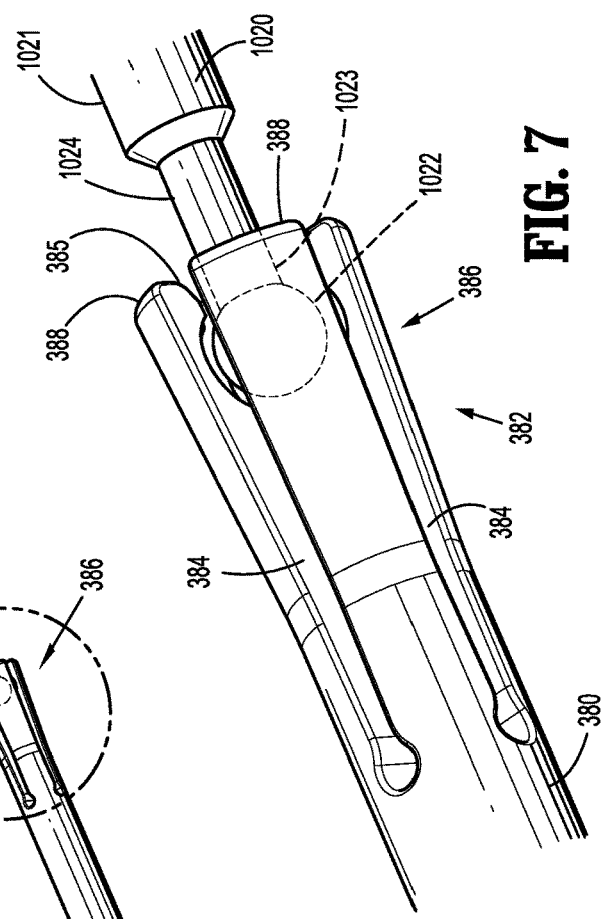

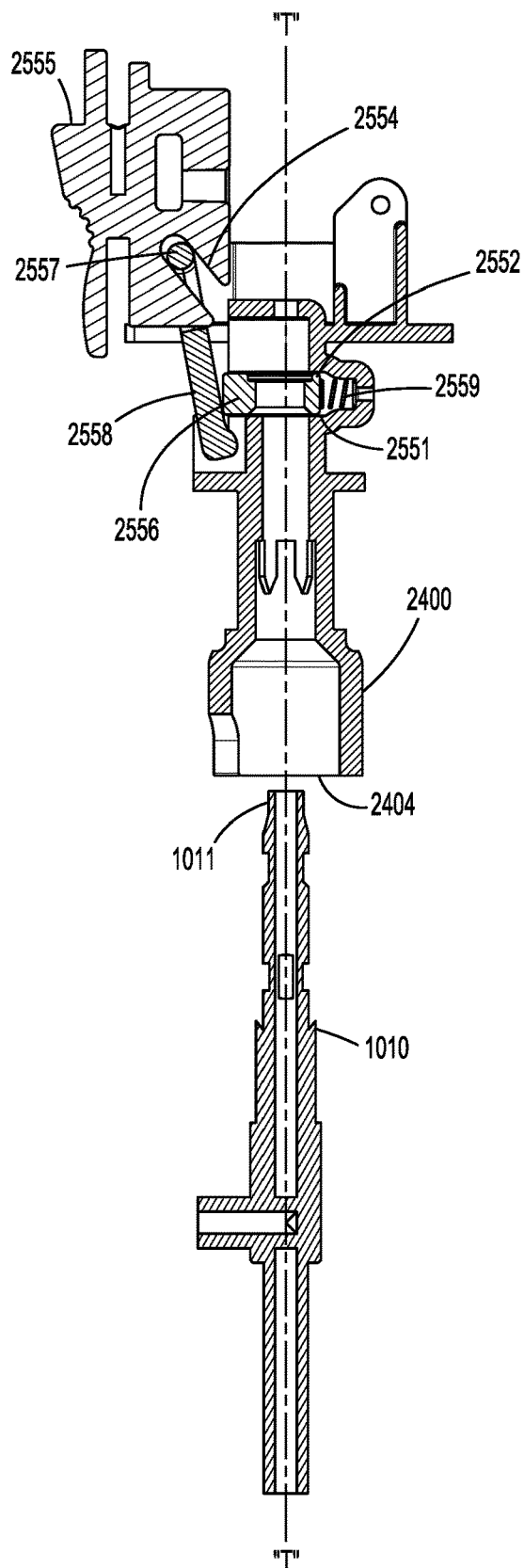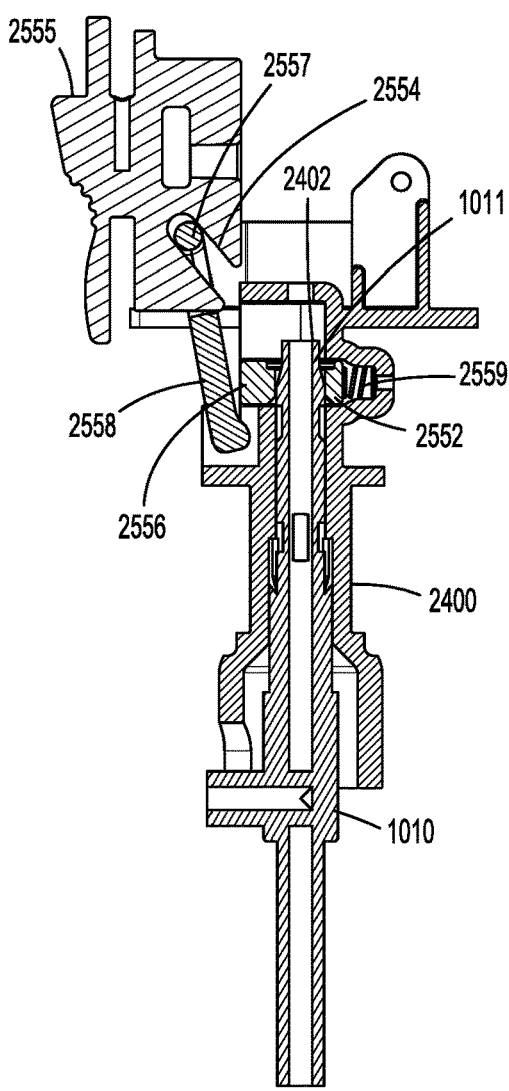
FIG. 18A
FIG. 18B

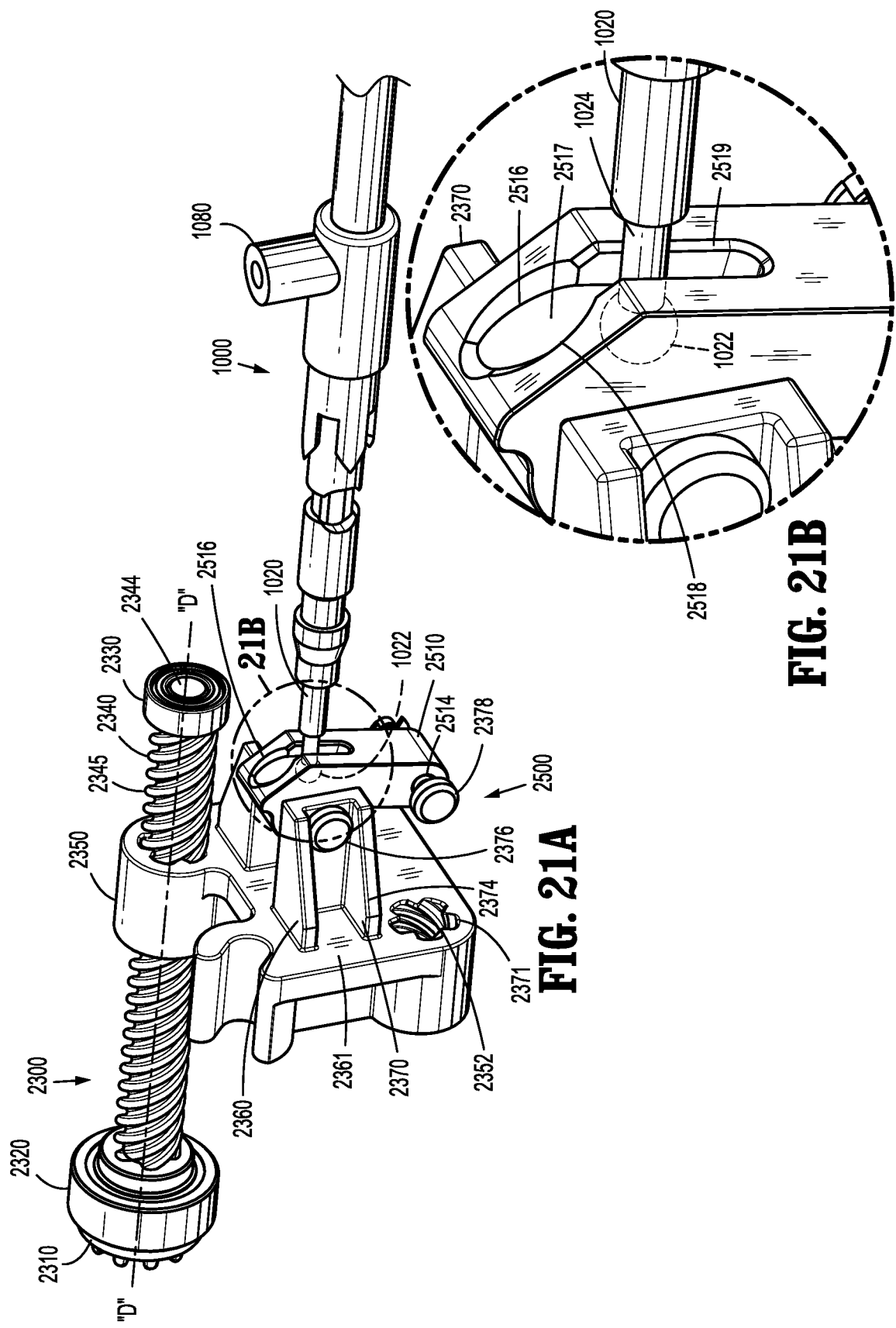

ROBOTIC SURGICAL SYSTEMS AND INSTRUMENT DRIVE ASSEMBLIES

CROSS-REFERENCE TO RELATED APPLICATIONS

This application is a Continuation Application which claims the benefit of and priority to U.S. patent application Ser. No. 16/065,924, filed on Jun. 25, 2018, which is a U.S. National Stage Application filed under 35 U.S.C. § 371(a) of International Patent Application Serial No. PCT/US2016/067469, filed Dec. 19, 2016, which claims the benefit of and priority to U.S. Provisional Patent Application Ser. No. 62/272,250, filed Dec. 29, 2015, the entire disclosure of which are incorporated by reference herein.

BACKGROUND

Robotic surgical systems have been used in minimally invasive medical procedures. Some robotic surgical systems include a console supporting a robot arm, and at least one end effector such as forceps or a grasping tool that is mounted to the robot arm via a wrist assembly. During a medical procedure, the end effector and the wrist assembly are inserted into a small incision (via a cannula) or a natural orifice of a patient to position the end effector at a work site within the body of the patient.

Cables extend from the robot console, through the robot arm, and connect to the wrist assembly and/or end effector. In some instances, the cables are actuated by means of motors that are controlled by a processing system including a user interface for a surgeon or clinician to be able to control the robotic surgical system including the robot arm, the wrist assembly and/or the end effector.

Prior to or during use of the robotic system, surgical instruments are selected and connected to an instrument drive assembly of each robot arm. For proper installation to be completed, certain connecting features of the surgical instrument must be matingly engaged to corresponding connecting features of the instrument drive assembly. Once these features are matingly engaged, the instrument drive assembly can drive the actuation of the surgical instrument. Accordingly, there is a need for instrument drive assemblies that not only provide quick and easy mechanical and electrical engagement with surgical instruments, but provide a means to couple to a variety of surgical instruments having unique end effectors attached thereto.

SUMMARY

The present disclosure relates to an instrument drive assembly including a housing assembly, a coupling tube, a coupling assembly, and a retention mechanism. The housing assembly supports a drive assembly therein. The coupling tube is supported at a distal end of the housing assembly and extends distally therefrom. The coupling assembly is supported in the housing assembly and is configured to releasably couple to an instrument drive shaft of a surgical instrument. The retention mechanism is configured to releasably couple to an instrument sleeve of the surgical instrument.

In embodiments, the drive assembly may include a drive screw, a drive nut, and a drive member. The drive screw includes a threaded portion, and the drive nut is threadably engaged with the threaded portion of the drive screw. Rotation of the drive screw results in longitudinal translation of the drive nut along a longitudinal axis of the drive screw. The drive member is coupled to the drive nut and extends distally therefrom, where longitudinal translation of the drive member drives a function of the surgical instrument.

It is disclosed that the coupling assembly may be slidably supported on the coupling tube, where the coupling tube interconnects the housing assembly and the coupling assembly and the drive member of the drive assembly is disposed within the coupling tube. It is further disclosed that the retention mechanism may be disposed within the coupling assembly.

In embodiments, the drive member further includes an engagement region disposed at a distal end thereof, where the engagement region is configured to releasably couple with a proximal end of the instrument drive shaft of the surgical instrument. It is disclosed that the engagement region of the drive member may define a socket and the instrument drive shaft may define a coupling ball disposed at a proximal end thereof. The socket may flex radially outward to facilitate coupling and uncoupling of the coupling ball of the instrument drive shaft to the engagement region of the drive member. It is further disclosed that the socket of the engagement region may further include a plurality of retention hooks disposed at a distal end and on an inner facing surface. The retention hooks are configured to facilitate retention of the coupling ball of the instrument drive shaft within the socket of the engagement region.

It is further disclosed that the retention mechanism may be biased into one of a locked configuration or an unlocked configuration with respect to the instrument sleeve of the surgical instrument. Further still, in the locked configuration the retention mechanism may be positioned on a longitudinal axis of the coupling tube, and in the unlocked configuration the retention mechanism may be positioned radially away from the longitudinal axis of the coupling tube, such that the retention mechanism comes into and out of abutment with the instrument sleeve. In an embodiment, the coupling assembly may be slidable along the coupling tube between a distal position and a proximal position with respect to the housing assembly. The retention mechanism may be in the locked configuration when the coupling assembly is in the distal position, and the retention mechanism may be in the unlocked configuration when the coupling assembly is in the proximal position. Further, the coupling assembly may be biased into one of the proximal or distal positions.

In an embodiment, the drive assembly includes a drive screw and a drive plate. The drive screw includes a threaded portion. The drive plate is threadingly engaged with the threaded portion of the drive screw such that rotation of the drive screw results in longitudinal translation of the drive plate along a longitudinal axis of the drive screw.

It is disclosed that the retention mechanism may be supported in the housing assembly and include a lock plate, a button, and a release arm. The lock plate is transitionable between a locked and unlocked configuration with respect to the instrument sleeve of the surgical instrument. The button is slidable between a first and second position. The release arm defines an engagement region configured to engage the button and an abutment region configured to abut the lock plate. With the button in the first position, the abutment region of the release arm is spaced away from the lock plate and the lock plate is in the locked configuration. With the button in the second position, the abutment region of the release arm is in abutment with the lock plate and the lock plate is in the unlocked configuration.

It is further disclosed that the button may define a cam slot including a first end and a second end, and the engagement region of the release arm is translatable along the cam slot of the button between the first and second ends of the cam slot. With the engagement region at the first end of the cam slot, the button is in the first position and the lock plate is in the locked configuration. With the engagement region at the second end of the cam slot, the button is in the second position and the lock plate is in the unlocked configuration.

It is disclosed that the lock plate may define a through-hole configured to receive the instrument sleeve therein. With the lock plate in the locked configuration, an inner surface of the through-hole abuts an outer surface of the instrument sleeve. With the lock plate in the unlocked configuration, the inner surface of the through-hole is spaced away from the outer surface of the instrument sleeve.

In an embodiment, the coupling assembly may include a drive link pivotably coupled to a distal portion of the coupling tube and fixedly coupled to a distally facing surface of the drive plate of the drive assembly. It is disclosed that the drive link may include a cam slot at a first end and a pin slot at a second end. A cam pin couples the drive link to the drive plate through the cam slot of the drive link, and a pin couples the drive link to the distal portion of the coupling tube through the pin slot of the drive link. It is further disclosed that proximal and distal translation of the drive plate of the drive assembly may drive the cam pin within the cam slot of the drive plate. Proximal and distal translation of the drive plate pivots the drive link about the pin and the pin slot between a locked position and an unlocked position, respectively.

It is disclosed that the drive link may further include a receiving region disposed on a distally facing surface. The receiving region includes a cavity, a port, and a channel. The cavity is configured to receive therein a coupling ball disposed at a proximal end of the instrument drive shaft. The port is configured to receive the coupling ball of the instrument drive shaft therethrough. The cavity is configured to receive a portion of the instrument drive shaft distal of the coupling ball therein. The receiving region of the drive link is configured to releasably couple the coupling ball of the instrument drive shaft to the drive plate.

It is further disclosed that with the drive link in the unlocked position, the drive plate of the drive assembly may be in a distal-most position such that the port of the receiving region of the drive link is coaxial with a longitudinal axis of the coupling tube. And with the drive link in the locked position, the drive plate of the drive assembly may be in a position proximal of the distal-most position such that the port of the receiving region is angled from the longitudinal axis of the coupling tube. It is disclosed that in the locked position the coupling ball of the instrument drive shaft is retained within the cavity of the receiving region and the portion of the instrument drive shaft distal of the coupling ball resides within the channel of the receiving region.

BRIEF DESCRIPTION OF THE DRAWINGS

Embodiments of the present disclosure are described herein with reference to the accompanying drawings, wherein:

FIG. 1A is a schematic illustration of a medical work station and operating console in accordance with the present disclosure;

FIG. 1B is a perspective view of a motor of a control device of the medical work station of FIG. 1A;

FIG. 6 is a perspective view of an inner drive assembly and a drive member of the instrument drive assembly of FIG. 2 coupled with an instrument drive shaft;

FIG. 7 is a perspective view of the area of detail of FIG. 6;

FIGS. 18A-18C are side views of a retention mechanism of the instrument drive assembly of FIG. 11 in various states of actuation during insertion of an instrument sleeve therein;

FIG. 21A is a perspective view of a drive assembly and a drive link of the instrument drive assembly of FIG. 11 coupled with the instrument drive shaft; and FIG. 21B is a perspective view of the area of detail of FIG. 21A.

DETAILED DESCRIPTION

Figure 2:
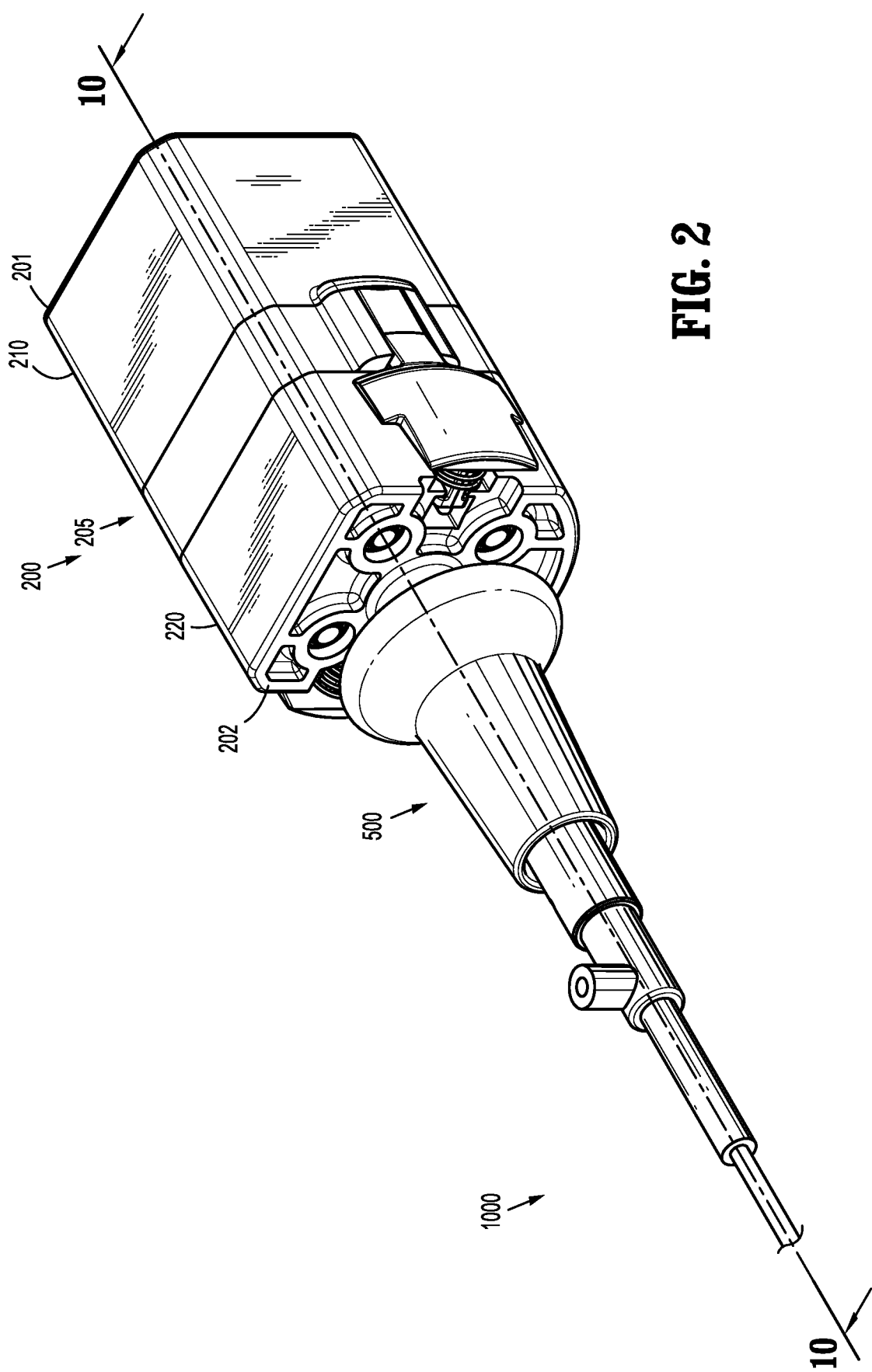
FIG. 2 is a perspective view of an instrument drive assembly in accordance with an embodiment of the present disclosure.

Embodiments of the presently disclosed instrument drive assemblies are described in detail with reference to the drawings, in which like reference numerals designate identical or corresponding elements in each of the several views. As is used in the art, the term "distal" refers to a position of an instrument, or portion thereof, which is farther from the user, and the term "proximal" refers to a position of an instrument, or portion thereof, which is closer to the user.

Referring initially to FIGS. 1A and 1B, a medical work station is shown generally as work station 1 and generally includes a plurality of robot arms 2, 3; a control device 4; and an operating console 5 coupled with control device 4. Operating console 5 includes a display device 6, which is set up in particular to display three-dimensional images; and manual input devices 7, 8, by means of which a person (not shown), for example a surgeon, is able to telemanipulate robot arms 2, 3 in a first operating mode, as known in principle to a person skilled in the art.

Each of the robot arms 2, 3 includes a plurality of members, which are connected through joints, and an instrument control unit 100, to which may be attached, for example, to an instrument drive assembly 200 of a surgical instrument 1000, the surgical instrument 1000 supporting an end effector (not shown) including, for example, a pair of jaw members, electrosurgical forceps, cutting instruments, or any other endoscopic, or open, surgical devices. For a detailed discussion and illustrative examples of the construction and operation of an end effector for use with instrument control unit 100, reference may be made to commonly owned International Patent Application No. PCT/US14/61329, filed on Oct. 20, 2014 and entitled "Wrist and Jaw Assemblies for Robotic Surgical Systems," the entire content of which is incorporated herein by reference.

Robot arms 2, 3 may be driven by electric drives (not shown) that are connected to control device 4. Control device 4 (e.g., a computer) is set up to activate the drives, in particular by means of a computer program, in such a way that robot arms 2, 3, instrument control units 100, and thus the surgical instruments 10 execute a desired movement or articulation according to a movement defined by means of manual input devices 7, 8. Control device 4 may also be set up in such a way that it regulates the movement of robot arms 2, 3 and/or of the drives.

Medical work station 1 is configured for use on a patient 13 lying on a patient table 12 to be treated in an open surgery, or a minimally invasive manner, by means of surgical instrument 1000. Medical work station 1 may also include more than two robot arms 2, 3, the additional robot arms likewise being connected to control device 4 and being telemanipulatable by means of operating console 5. An instrument control unit and a surgical instrument may also be attached to the additional robot arm. Medical work station 1 may include a database 14, in particular coupled to or with control device 4, in which pre-operative data from patient 13 and/or anatomical atlases, for example, may be stored.

For a detailed discussion of the construction and operation of medical work station 1 reference may be made to U.S. Patent Application Publication No. 2012/0116416, filed on Nov. 3, 2011 and entitled "Medical Workstation," (now U.S. Pat. No. 8,828,023) the entire content of which is incorporated herein by reference.

Control device 4 may control a plurality of motors (e.g., "M1"-"M6"). Motors "M" may be part of instrument control unit 100 and/or disposed externally of instrument control unit 100. Motors "M" (e.g., motors "M" being located externally of instrument control unit 100) may be configured to rotate a crown gear "CG" (FIG. 1B), or the like, that is keyed to or non-rotatably supported on a rotatable shaft of at least some of motors "M," or act on a cable to draw in or let out length of cable to actuate robot arms 2, 3. In use, as motors "M" are driven, the rotation of crown gear(s) "CG" effects operation, movement, and/or articulation of instrument drive assembly 200 of surgical instrument 1000, and an end effector attached thereto, as discussed below. It is further envisioned that at least one motor "M" receives signals wirelessly (e.g., from control device 4). It is contemplated that control device 4 coordinates the activation of the various motors (Motor 1 . . . n) to coordinate an operation, movement, and/or articulation of robot arms 2, 3 and/or surgical instrument 1000. It is envisioned that each motor may corresponds to a separate degree of freedom of robot arms 2, 3, and/or surgical instrument 1000 engaged with instrument control unit 100. It is further envisioned that more than one motor, including every motor (Motor 1 . . . n), is used for each degree of freedom.

Turning now to FIGS. 2-13, instrument drive assembly 200 is configured to engage instrument control unit 100 at a proximal end 201 thereof and couple to surgical instrument 1000 at a distal end 202 thereof, where surgical instrument 1000 extends distally from instrument drive assembly 200, as described herein. Instrument drive assembly 200 is configured to transfer rotational movement supplied by instrument control unit 100 (e.g., via motors "M") into longitudinal movement of a drive member 380 (FIGS. 5A and 7-10) to effect various functions of surgical instrument 1000.

Figure 4:
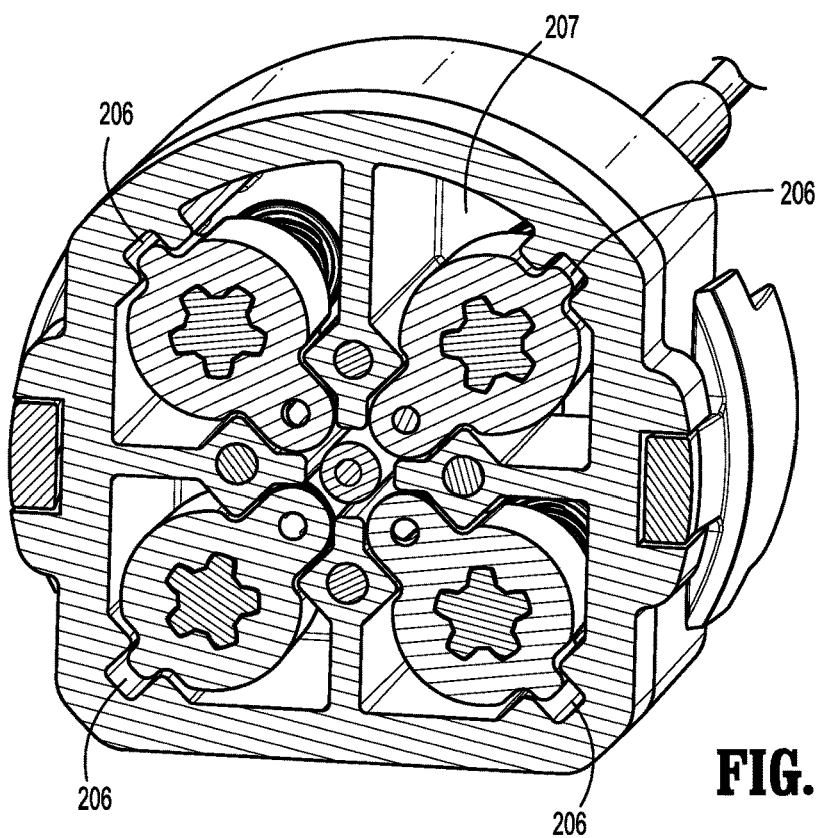
FIG. 4 is a perspective, cross-sectional view of the instrument drive assembly of FIG. 2 taken along the section line 4-4 of FIG. 3.
Figure 5A:
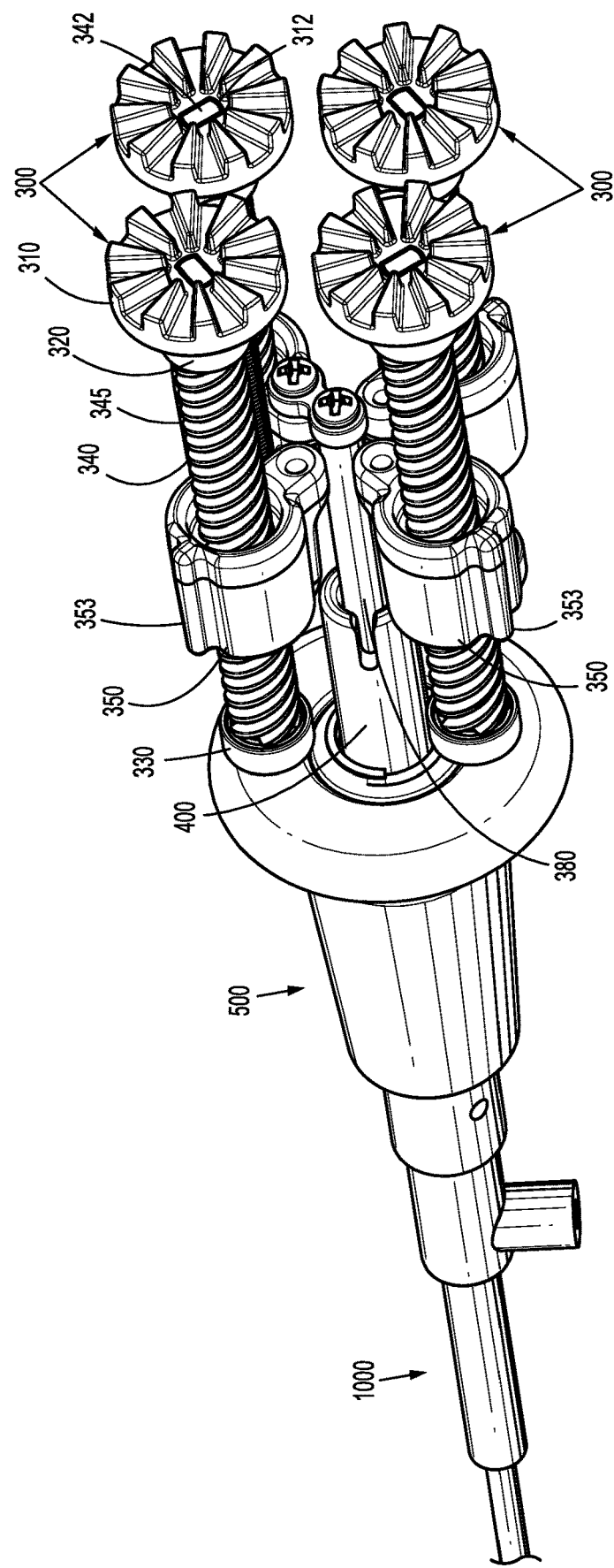
FIG. 5A is a rear perspective view of the instrument drive assembly of FIG. 2 with various parts removed therefrom.
Figure 5B:
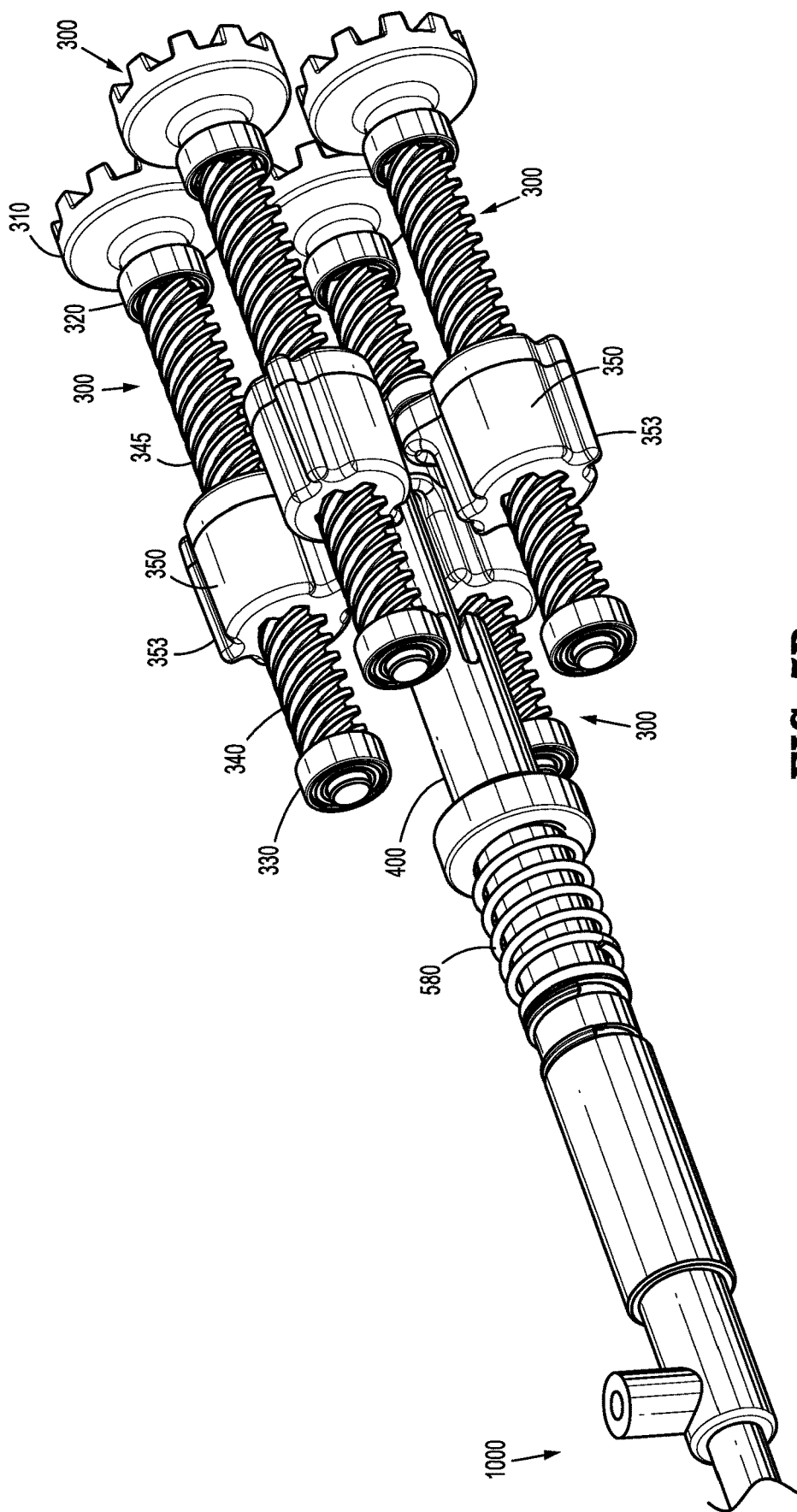
FIG. 5B is a front perspective view of the instrument drive assembly of FIG. 5A.

With reference to FIGS. 2 and 8-10, instrument drive assembly 200 includes a housing assembly 205 which includes a proximal housing 210 and a distal housing 220. Proximal housing 210 and distal housing 220 are releasably couplable to each other, which may facilitate assembly of instrument drive assembly 200, and which may facilitate access, repair, and/or replacement of parts housed at least partially therein. Housing assembly 205 defines at least one bore 207 (as best illustrated in FIG. 4) for housing an inner drive assembly 300 (FIG. 7) therein. It is envisioned that housing assembly 205 includes four separate bores 207, where each bore 207 is at least partially separated from each other and where each bore 207 is configured to house a separate single inner drive assembly 300. Additionally, as discussed below, each respective bore 207 includes a longitudinally-extending channel 206 (e.g., four channels 206) therein (FIG. 4). Each channel 206 is configured to slidingly accept a rail 353 of a drive nut 350 (FIG. 7), as described below. In the illustrated embodiment, instrument drive assembly 200 includes four inner drive assemblies, however instrument drive assembly 200 may include more (e.g., five or six) or fewer (e.g., three) inner drive assemblies without departing from the scope of the present disclosure. It is further envisioned that all inner drive assemblies, or a select number of inner drive assemblies, may be coupled to one or more respective drive members 380, whereas the exemplary illustration provides a singular inner drive assembly 300 inner inner drive assembly 300 coupled to drive member 380, as described below.

Figure 3:
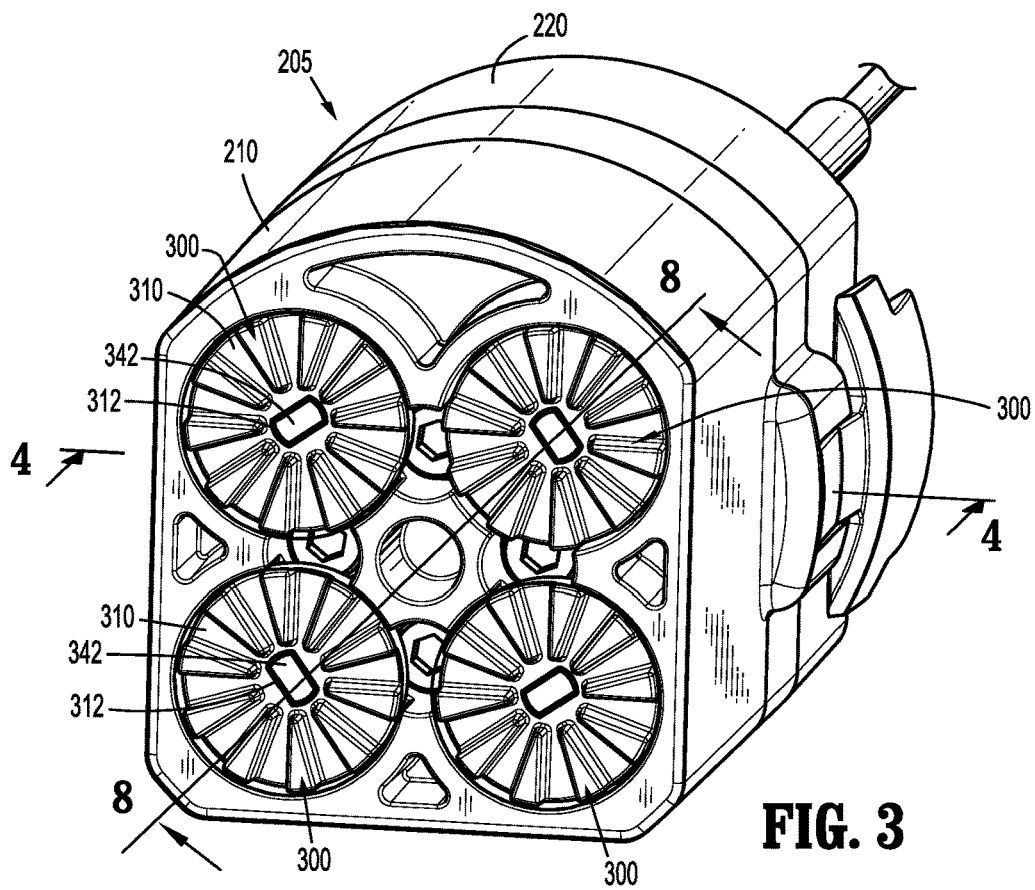
FIG. 3 is rear perspective view of the instrument drive assembly of FIG. 2.

With reference to FIGS. 3, 4 and 7, each inner drive assembly 300 includes a proximal gear 310, a proximal bearing 320, a distal bearing 330, a drive screw 340, and drive nut 350. Drive screw 340 includes a proximal portion 342, a proximal shaft 343, a threaded portion 345 and a distal shaft 344, and defines a longitudinal axis "A-A" extending through a radial center thereof (FIG. 7). Proximal gear 310 is configured to engage, directly or indirectly, with an instrument control gear (e.g., crown gear "CG" of motor "M") of instrument control unit 100, such that rotation of crown gear "CG" causes a corresponding rotation of proximal gear 310. Proximal gear 310 may be a crown gear "CG" that is configured to mate with and/or mesh with crown gear "CG" of motor "M." Proximal gear 310 includes an aperture 312 extending longitudinally therethrough configured to mechanically engage proximal portion 342 of drive screw 340. As shown, aperture 312 and proximal portion 342 of drive screw 340 have corresponding, non-circular cross-sections, such that proximal gear 310 and drive screw 340 are keyed to one another, which results in a rotationally fixed connection therebetween. Rotation of proximal gear 310 causes drive screw 340 to rotate about longitudinal axis "A" in a corresponding direction and rate of rotation.

Figure 9:
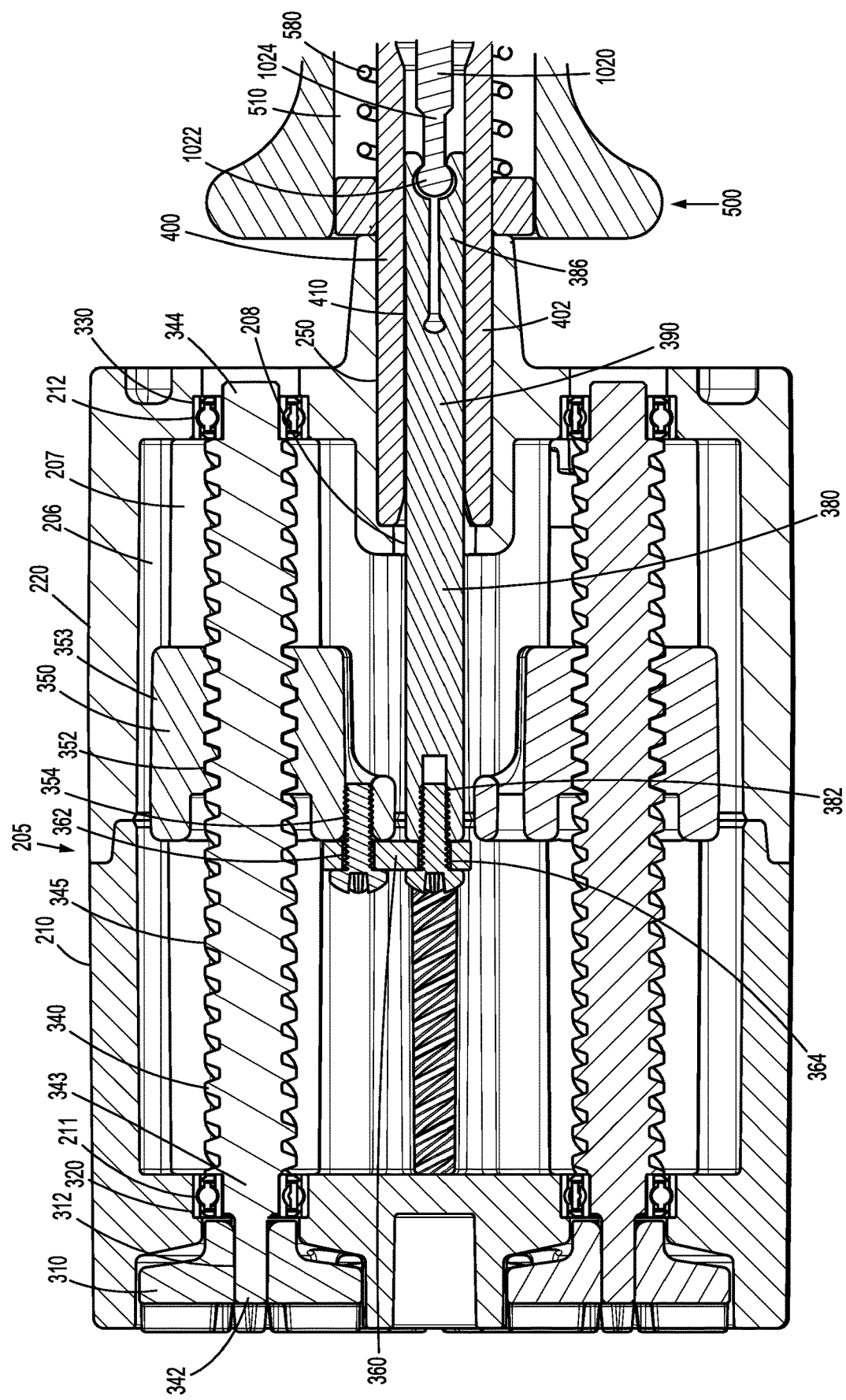
FIG. 9 is a side view of the area of detail of FIG. 8A.
Figure 10:
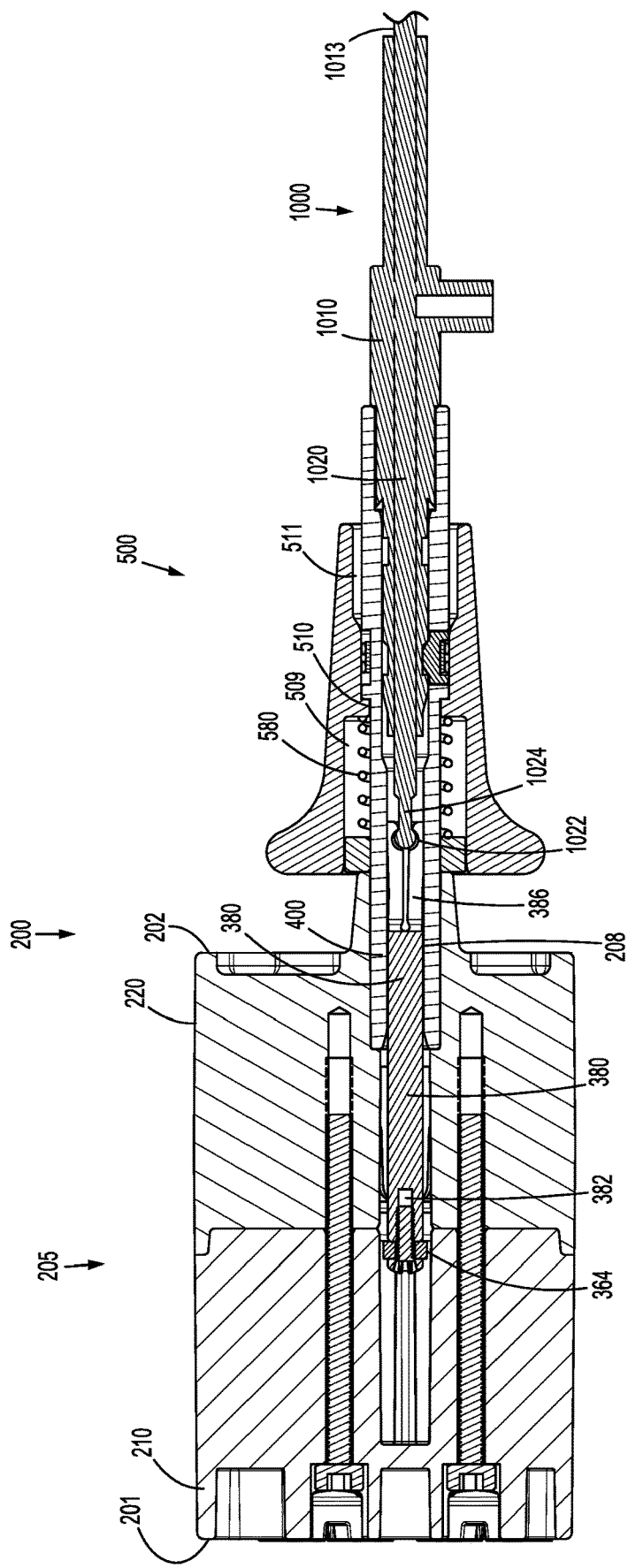
FIG. 10 is a side, cross-sectional view of the instrument drive assembly of FIG. 2 taken along section line 10-10 of FIG. 2.

Drive nut 350 includes a threaded aperture 352 extending longitudinally therethrough, which is configured to mechanically engage threaded portion 345 of drive screw 340. That is, drive nut 350 and drive screw 340 are threadingly engaged with each other. Drive nut 350 includes a rail 353 extending longitudinally along an outer surface thereof and is configured to be slidably disposed in the longitudinally extending channel 206 formed in bore 207 of housing assembly 205 (FIGS. 6 and 9). Rail 353 of drive nut 350 cooperates with channel 206 of bore 207 to inhibit or prevent drive nut 350 from rotating about longitudinal axis "A" as drive screw 340 is rotated. Accordingly, drive nut 350 is configured to be positioned on drive screw 340 in a manner such that rotation of drive screw 340 causes longitudinal translation of drive nut 350. More specifically, rotation of proximal gear 310 in a first direction (e.g., clockwise) causes drive screw 340 to rotate in a corresponding first direction and drive nut 350 to translate in a first longitudinal direction (e.g., proximally) with respect to proximal gear 310, and rotation of proximal gear 310 in a second direction (e.g., counter-clockwise) causes drive screw 340 to rotate in a corresponding second direction and drive nut 350 to translate in a second longitudinal direction (e.g., distally) with respect to proximal gear 310.

Drive nut 350 further defines a bore-hole 354 laterally offset from, and parallel to, threaded aperture 352. It is contemplated that bore-hole 354 may define threads on an inner surface such that drive nut 350 may be coupled to drive member 380, as discussed below.

As illustrated (FIGS. 5A and 9), the drive nut 350 of one inner drive assembly 300 is coupled to drive member 380, where drive member 380 may define, for example, a drive bar or push bar, as described below. A link bar 360 defining two bore-holes 362, 364 laterally offset from one another is configured to couple drive nut 350 and drive member 380 (FIGS. 7 and 9). It is contemplated that a respective link bar 360 may be provided for each respective drive assembly 300, or a select number of link bars 360 may be provided for a select number of inner drive assemblies, such that each drive nut 350 of the respective inner drive assembly 300 may be coupled to either a respective drive member 380, or the same drive member 380.

Link bar 360 may be monolithically formed with drive nut 350, drive member 380, or both drive nut 350 and drive member 380, such that drive nut 350, link bar 360, and drive member 380 consist of one unitary body. Alternatively, drive nut 350, link bar 360, and drive member 380 may be fastened by any mechanical means known in the art, such as, for example, by utilizing a screw or bolt. In such an embodiment, bore-holes 362, 364 of link bar 360 may define threads on an inner surface thereof, such that a bolt or screw may be threadably engaged between link bar 360 and drive nut 350, and link bar 360 and drive member 380. More specifically, a screw may be threadably engaged through bore-hole 362 of link bar 360 and bore-hole 354 of drive nut 350, thereby securing link bar 360 thereto. An additional screw may be threadably engaged through bore-hole 364 of link bar 360 and a bore-hole 382 of drive member 380, thereby securing link bar 360 thereto. With drive nut 350 coupled to drive member 380, it should be appreciated that proximal and distal translation of drive nut 350 with respect to proximal gear 310 results in a corresponding proximal or distal translation of drive member 380, as discussed in further detail below.

With inner drive assembly 300 and housing assembly 205 assembled, proximal bearing 320 is disposed in a proximal bearing cavity 211 of proximal housing 210, and distal bearing 330 is disposed in a distal bearing cavity 212 of distal housing 220 (FIG. 9). Each of proximal bearing 320 and distal bearing 330 facilitate rotation of drive screw 340 with respect to housing assembly 205, and may further serve as proximal and distal stops, respectively, for drive nut 350.

Drive member 380 extends distally from link bar 360, through a central bore 208 (FIGS. 8-10) of housing assembly 205, and is configured to mechanically engage a portion of surgical instrument 1000, as described herein. Longitudinal translation of drive member 380 is configured to drive a function of the end effector disposed at a distal end of surgical instrument 1000. For example, surgical instrument 1000 may include a first end effector configured such that distal translation of drive member 380 directs a pair of jaw members of a clamping device to move into approximation with respect to one another, and proximal translation of drive member 380 may be configured to move at least one jaw member into a spaced apart position with respect to the other jaw member. It should be appreciated that proximal and distal translation of drive member 380 may be configured to effect operation, articulation, or actuation of any number of unique end effectors of a respective surgical instruments 1000, such as, for example, actuation of a cutting blade and/or initiation of the delivery of electrosurgical energy to tissue, etc.

Figure 8A:
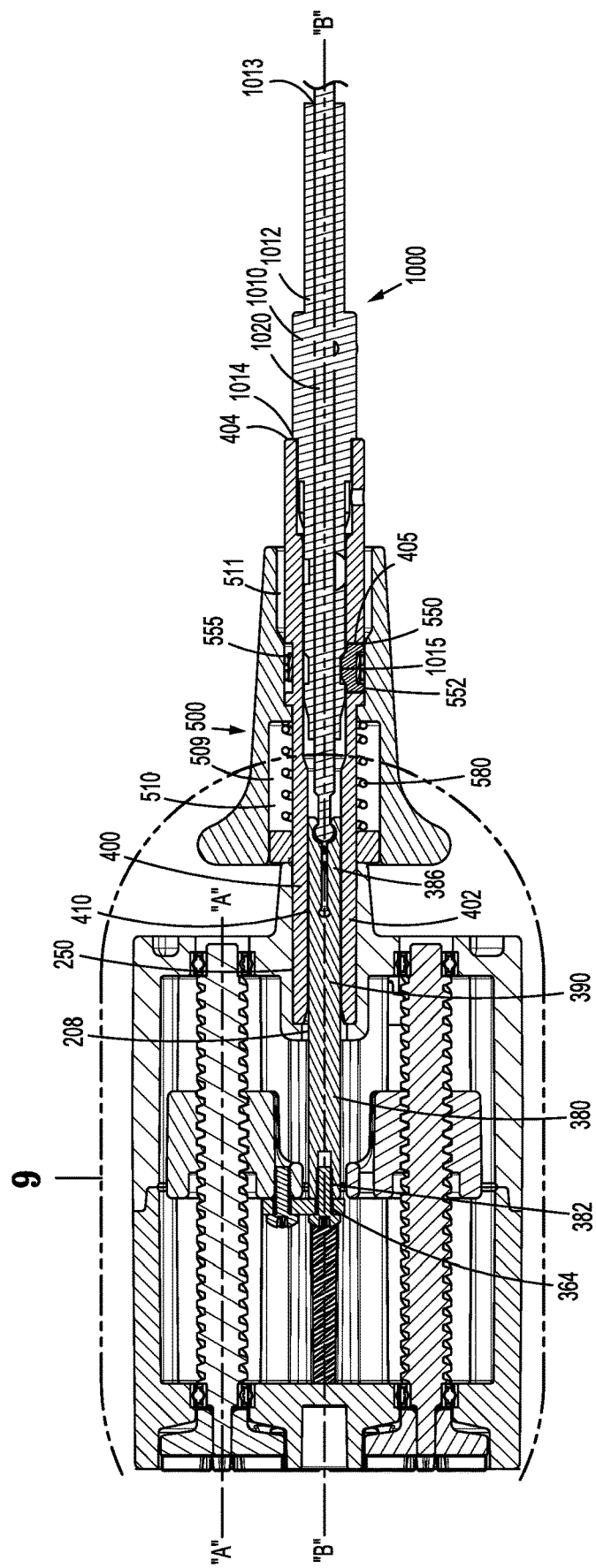
FIG. 8A is a side, cross-sectional view of the instrument drive assembly of FIG. 2 taken along section line 8-8 of FIG. 3 with a coupling assembly in a distal position.
Figure 8B:
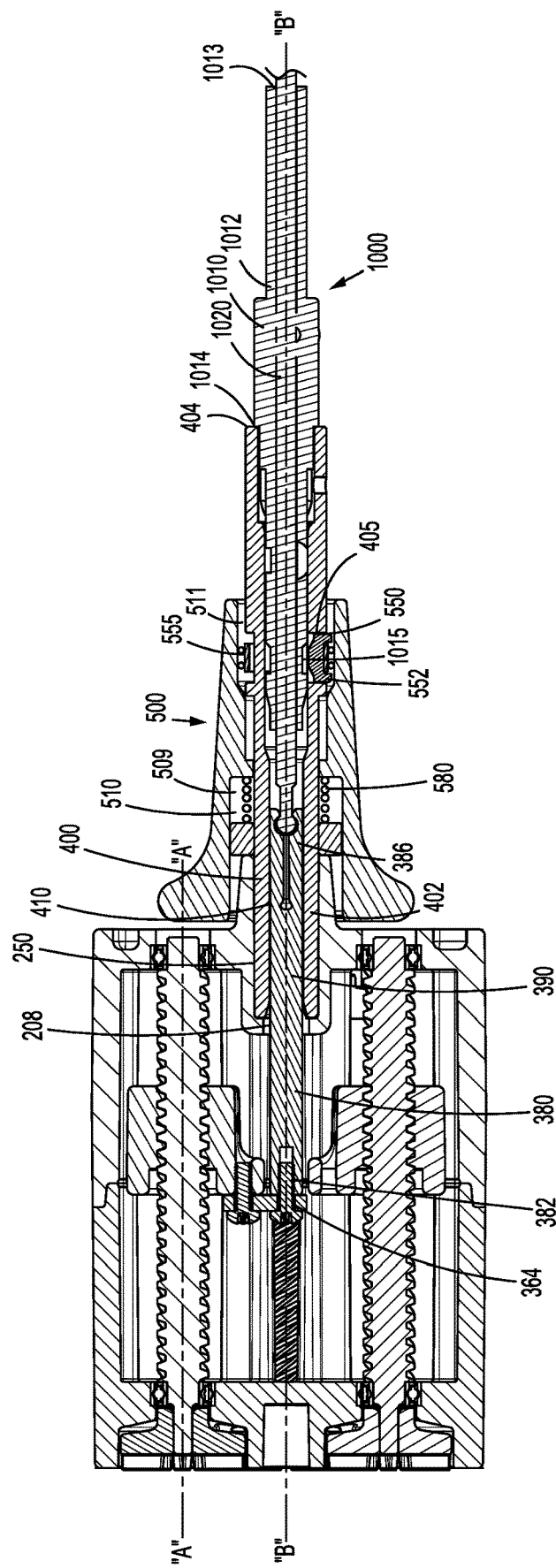
FIG. 8B is a side, cross-sectional view of the instrument drive assembly of FIG. 2 taken along section line 8-8 of FIG. 3 with the coupling assembly in a proximal position.

With reference to FIGS. 2, 8A and 8B, the engagement of surgical instrument 1000 to instrument drive assembly 200, and more particularly to housing assembly 205 and drive member 380, will be described. Housing assembly 205 further includes a coupling assembly 500 disposed distally of distal end 202 of housing assembly 205. Coupling assembly 500 serves to releasably couple surgical instrument 1000 to housing assembly 205, and releasably couple an instrument drive shaft 1020 of surgical instrument 1000 to drive member 380 (FIGS. 8A-10).

Briefly, surgical instrument 1000 may include an instrument sleeve 1010, which defines a longitudinally extending lumen 1012 configured to receive at least a portion of instrument drive shaft 1020 therein, and an end effector (not shown) coupled to, and disposed at, a distal end of instrument drive shaft 1020. Instrument drive shaft 1020 is configured to translate longitudinally within the lumen 1012 of instrument sleeve 1010, such that instrument drive shaft 1020 controls actuation, articulation, and/or firing of the end effector, such as, for example, approximation of first and second jaw members to grasp tissue therebetween, advancement of a knife blade to sever tissue, articulation of the orientation and/or direction of the end effect, and/or any other function described herein or known in the art. More specifically, through proximal and distal translation of instrument drive shaft 1020, with respect to instrument sleeve 1010, instrument drive shaft 1020 actuates the end effector. For example, translation of instrument drive shaft 1020 in a first direction (e.g., distally), may cause a first and second jaw member (not shown) to move into a spaced apart configuration with respect to one another such that tissue may be disposed therebetween, and translation of instrument drive shaft 1020 in a second direction (e.g., proximally) may cause the first and second jaw members to move into an approximated configuration with respect to one another such that tissue disposed therebetween is securely grasped. It should be appreciated that the above examples are exemplary in nature, and the instrument drive shaft 1020 and end effector may be configured to actuate in any number of ways.

With reference to FIGS. 8A-10, a coupling tube 400 serves to interconnect housing assembly 205 and coupling assembly 500. Coupling tube 400 includes a proximal portion 402 disposed in a distal cavity 250 of distal housing 220 of housing assembly 205, and extends distally therefrom. Distal cavity 250 is coaxial with central bore 208 of housing assembly 205 and is configured to receive a diameter of coupling tube 400 therein. As illustrated, a longitudinally extending lumen 410 of coupling tube 400 is configured to slidingly receive a distal portion 390 of drive member 380 therein, such that a portion of drive member 380 is translatable therethrough. Coupling tube 400 extends distally through a longitudinal cavity 510 of coupling assembly 500, such that coupling assembly 500 is slidably supported thereon, as discussed below. As such, it should be appreciated that central bore 208 of housing assembly 205, drive member 380, coupling tube 400, and longitudinal cavity 510 of coupling assembly 500 are coaxial.

Coupling assembly 500 is longitudinally translatable along coupling tube 400 between a proximal position (FIG. 8B) and a distal position (FIG. 8A), with respect to housing assembly 205. As will be described below, in the proximal position, instrument sleeve 1010 of surgical instrument 1000 is releasably coupled to coupling assembly 500 and instrument drive shaft 1020 is releasably coupled to drive member 380; and in the distal position, instrument sleeve 1010 is securely coupled to coupling assembly 500 and instrument drive shaft 1020 is securely coupled to drive member 380. It is envisioned that coupling assembly 500 may additionally aid alignment of instrument drive shaft 1020 and drive member 380 during coupling.

More specifically, instrument sleeve 1010 of surgical instrument 1000 is slidably inserted into a distal opening 404 of coupling tube 400. A notch 1014 extending outward from an outer surface of instrument sleeve 1010 is configured to abut distal end 404 of coupling tube 400 when instrument sleeve 1010 of surgical instrument 1000 is fully inserted therein. It is further envisioned that coupling assembly 500 provides a retention mechanism 550, such that instrument sleeve 1010 of surgical instrument 1000 is releasably retained or secured within coupling tube 400, and thus, releasably secured to coupling assembly 500 and thus housing assembly 205. As will be described herein below, retention mechanism 550 is transitionable between a locked configuration and an unlocked configuration.

It is contemplated that as instrument sleeve 1010 of surgical instrument 1000 slides proximally within coupling tube 400, a button or biasing member 552 disposed in longitudinal cavity 510 of coupling assembly 500 is configured to engage a recess 1015 disposed on the outer surface of instrument sleeve 1010. As best illustrated in FIGS. 8A and 8B, button 552 may be disposed in longitudinal cavity 510 such that it resides in a radial cavity 405 extending through a portion of coupling tube 400. It should be appreciated that button 552 translates radially inward with respect to a longitudinal axis "B" (FIG. 8A) of coupling tube 400 to engage instrument sleeve 1010 of surgical instrument 1000 in the locked configuration, and translates radially outward (FIG. 8B) to disengage instrument sleeve 1010 in the unlocked configuration. With button 552 in the locked configuration, button 552 is engaged with recess 1015 such that longitudinal translation of instrument sleeve 1010 of surgical instrument 1000, within coupling tube 400, is inhibited, and in the unlocked configuration, button 552 is disengaged from recess 1015 such that instrument sleeve 1010 freely slides proximally and distally within coupling tube 400. Radial cavity 405 may be transverse to the longitudinal axis "B" of coupling tube 400, such that when button 552 actuates between the locked and unlocked configurations, button 552 translates perpendicular to coupling tube 400, and instrument sleeve 1010 of surgical instrument 1000 inserted therein. Alternatively, radial cavity 405 and button 552 may be configured such that button 552 translates at an angle with respect to the longitudinal axis "B" of coupling tube 400, such that button 552 slides into and out of engagement with recess 1015 of instrument sleeve 1010 of surgical instrument 1000.

It is further contemplated that retention mechanism 550 may be disposed proximally of distal end 404 of coupling tube 400, such that instrument sleeve 1010 of surgical instrument 1000 slides within coupling tube 400 in a proximal direction an initial distance prior to engaging button 552 of retention member 550. It is further envisioned that a biasing member 555 may be disposed within longitudinal cavity 510 of coupling assembly 500 which is configured to bias button 552 into the locked configuration. Biasing member 555 may include a spring element disposed within radial cavity 405 in abutment with both button 552 and longitudinal cavity 510 and/or coupling tube 400. With button 552 biased into the locked configuration, as instrument sleeve 1010 slides proximally, the bias member 555 is overcome and button 552 is urged radially outward into the unlocked configuration. Once instrument sleeve 1010 is translated proximally the initial distance, recess 1015 is aligned with button 552, permitting button 552 to return to the locked configuration.

With reference to FIGS. 7-9, engagement of drive member 380 of inner drive assembly 300 and instrument drive shaft 1020 of surgical instrument 1000 will be discussed. As best illustrated in FIG. 7, a distal portion 382 of drive member 380 defines an engagement region 386. Engagement region 386 of drive member 380 includes a plurality of longitudinally extending slits 384, where each slit 384 is disposed about a circumference of a distal end 388 of drive member 380, and extends proximally therefrom along a portion of drive member 380. As a result of the plurality of longitudinally extending slits 384, the engagement region 386 of drive member 380 forms an expandable leaf feature, and may thus flex radially outward to facilitate the releasable coupling of instrument drive shaft 1020 of surgical instrument 1000 therewith. It is further envisioned that an inner surface of retention region 386 of drive member 380 may define an arcuate cavity, i.e., a socket joint, configured to receive a coupling ball 1022 of instrument drive shaft 1020 of surgical instrument 1000, as described below. It is contemplated that engagement region 386 of drive member 380 further includes retention hooks 385 disposed at the distal end 388 of drive member 380 on an inner facing surface thereof, where retention hooks 385 facilitate retention of coupling ball 1022 of instrument drive shaft 1020 therein.

More specifically, instrument drive shaft 1020 of surgical instrument 1000 includes a neck 1024 extending proximally from a proximal end 1021 thereof, where coupling ball 1022 (shown in phantom in FIG. 7) is disposed at a proximal end 1023 of neck 1024. It is contemplated that coupling ball 1022, neck 1024, and instrument drive shaft 1020 may be coupled by any means known in the art and/or may be monolithically formed. A diameter of neck 1024 may be smaller than a diameter of coupling ball 1022, such that when coupling ball 1022 is received within retention region 386 of drive member 380, retention hooks 385 of retention region 386 surround and enclose coupling ball 1022, thus providing further securement therein. When coupling drive member 380 of inner drive assembly 300 and instrument drive shaft 1020 of surgical instrument 1000, the coupling ball 1022 of instrument drive shaft 1020 is brought into approximation with retention region 386 of drive member 380. As instrument drive shaft 1020 is moved proximally with respect to drive member 380, coupling ball 1022 urges retention region 386 to flex radially outward, such that coupling ball 1022 is received therein. With coupling ball 1022 received within retention region 386, coupling ball 1022 is thereby releasably coupled to drive member 380. With drive member 380 coupled to instrument drive shaft 1020, proximal and distal translation of drive member 380 directs a corresponding proximal and distal translation of instrument drive bar 1020.

To uncouple instrument drive shaft 1020 of surgical instrument 1000 from drive member 380 of inner drive assembly 300, instrument drive bar 1020 is moved distally with respect to drive member 380, such that coupling ball 1022 is pulled out of, and released from, retention region 386.

As referenced above, coupling assembly 500 of housing assembly 205 is slidably supported on coupling tube 400 between a proximal position and a distal position with respect to housing assembly 205. With coupling assembly 500 in the distal position, i.e., a locked configuration, button 552 of retention mechanism 550 is maintained in the locked configuration with respect to instrument sleeve 1010 of surgical instrument 1000, and with coupling assembly 500 in the proximal position, i.e., an unlocked configuration, button 552 may be actuated into the unlocked configuration with respect to instrument sleeve 1010. Thus, translation of coupling assembly 500 permits the locking and unlocking of instrument sleeve 1010 of surgical instrument 1000.

It should be appreciated that a distal portion 511 of longitudinal cavity 510 of coupling assembly 500 defines a larger diameter, such that when coupling assembly 500 is in the proximal position, distal portion 511 of the longitudinal cavity 510 aligns with button 552, such that button 552 is disposed therein and thus permitted to translate radially outward into the unlocked configuration with respect to instrument sleeve 1010 of surgical instrument 1000.

It is contemplated that coupling assembly 500 further includes a biasing element 580, such that coupling assembly 500 is biased into the distal position, i.e., the locked configuration. In an exemplary illustration, biasing element 580 is disposed in a proximal portion 509 of longitudinal cavity 510, however it is envisioned that biasing element 580 may be disposed in any portion of coupling assembly 500. More specifically, when uncoupling surgical instrument 1000 from instrument drive assembly 200, coupling assembly 500 is translated proximally, such that button 552 aligns with the distal portion 511 of the longitudinal cavity 510 of coupling assembly 500, and such that button 552 may translate radially outward, out of engagement with recess 1015 of instrument sleeve 1010. With button 552 disengaged, instrument sleeve 1010 is permitted to slide distally to be removed from coupling tube 400, and instrument drive assembly 200.

During use, with instrument drive assembly 200 in an active state (i.e., when motor(s) "M" of instrument control unit 100 rotate proximal gear(s) 310), rotation of proximal gear 310 results in a corresponding rotation of drive screw 340. Rotation of drive screw 340 causes longitudinal translation of drive nut 350 due to the engagement between threaded portion 345 of drive screw 340 and threaded aperture 352 of drive nut 350. As discussed above, the direction of longitudinal translation of drive nut 350 is determined by the direction of rotation of proximal gear 310, and thus drive screw 340. With instrument sleeve 1010 of surgical instrument 1000 coupled to coupling assembly 500, and instrument drive shaft 1020 coupled to drive member 380, rotation of proximal gear 310 directs linear translation of drive member 380 and instrument drive shaft 1020. More specifically, rotation of proximal gear 310 in a first direction (e.g., clockwise) causes drive screw 340 to rotate in a corresponding first direction and drive nut 350 to translate in a first longitudinal direction (e.g., proximally) with respect to proximal gear 310, which translates drive member 380 and instrument drive shaft 1020 in a corresponding first longitudinal direction (e.g., proximally). Rotation of proximal gear 310 in a second direction (e.g., counter-clockwise) causes drive screw 340 to rotate in a corresponding second direction and drive nut 350 to translate in a second longitudinal direction (e.g., distally) with respect to proximal gear 310, which translates drive member 380 and instrument drive shaft 1020 in a corresponding second longitudinal direction (e.g., distally).

With reference to FIGS. 11-21B, an alternate embodiment of instrument drive assembly 200, in accordance with the present disclosure, will be described with reference to instrument drive assembly 2000. As discussed below, instrument sleeve 1010 and instrument drive shaft 1020 of surgical instrument 1000 are also releasably couplable to instrument drive assembly 2000.

Figure 11:
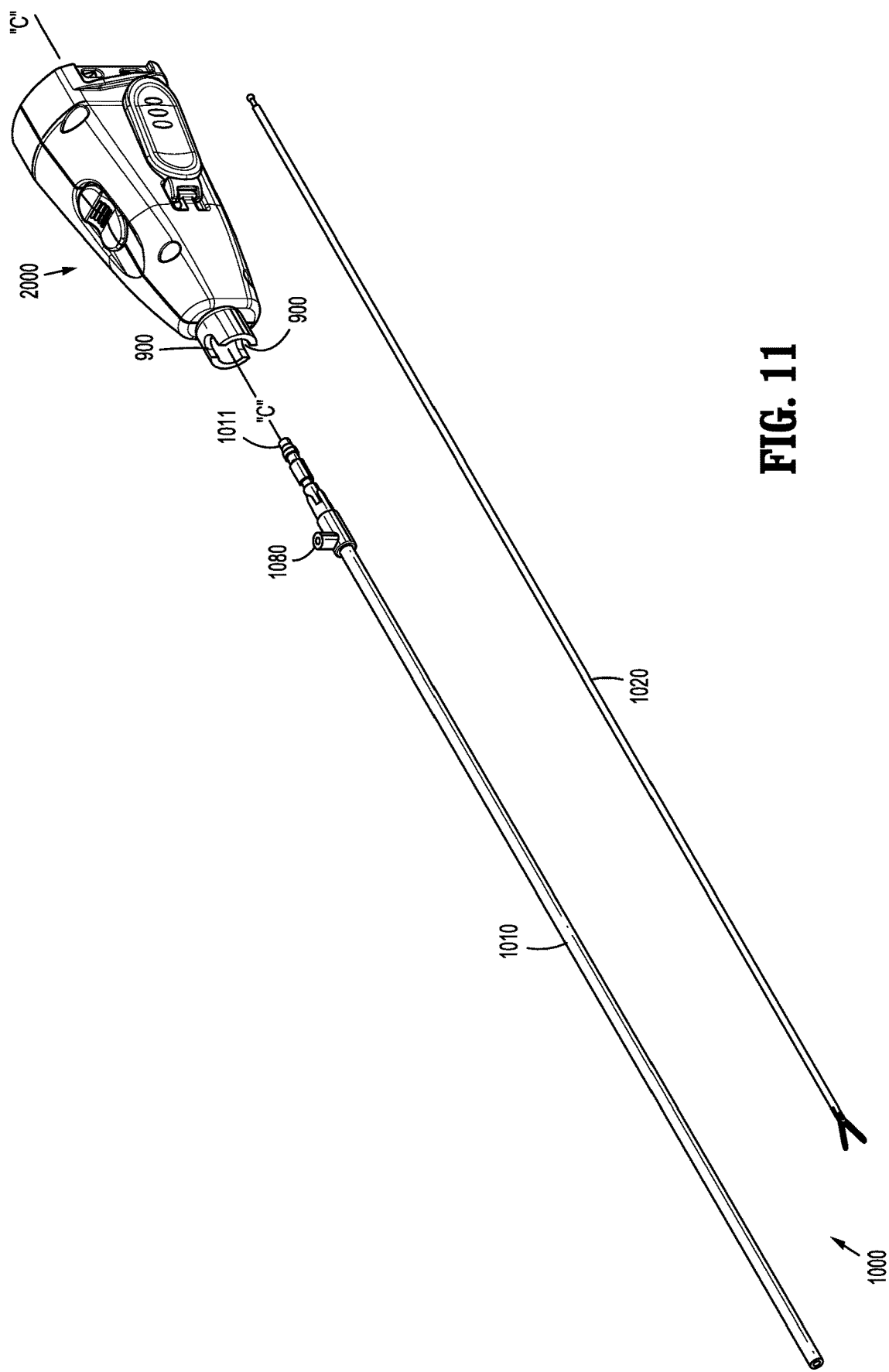
FIG. 11 is a perspective view of an instrument drive assembly in accordance with another embodiment of the present disclosure.
Figure 12:
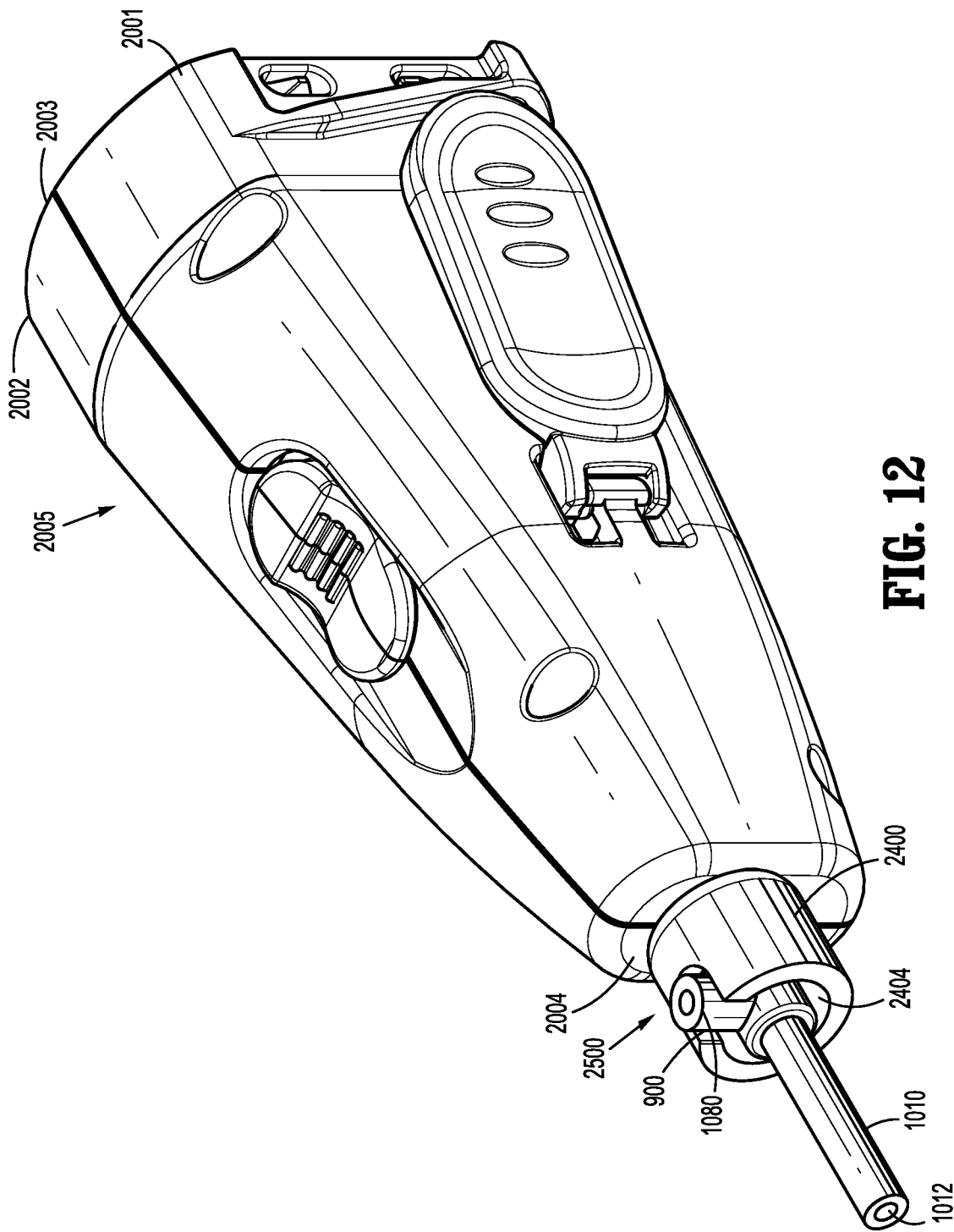
FIG. 12 is a front perspective view of the instrument drive assembly of FIG. 11.
Figure 13:
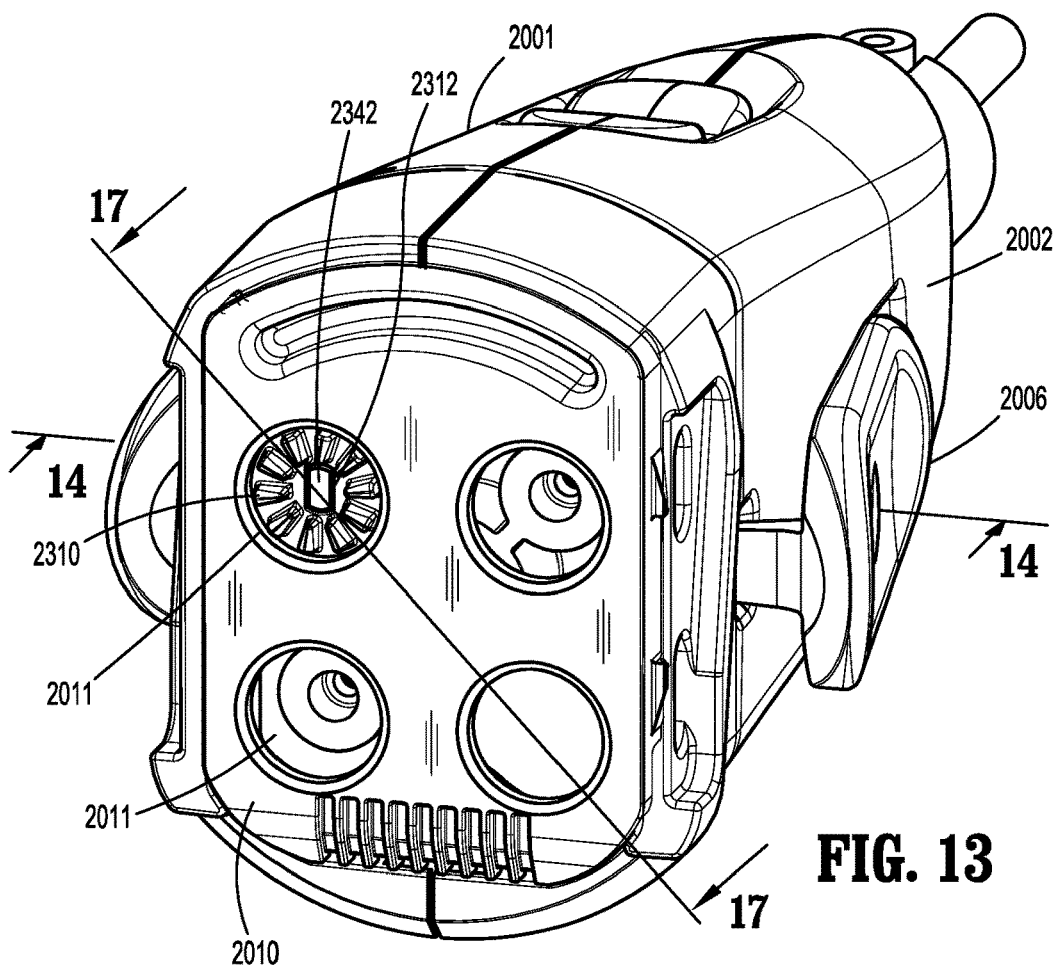
FIG. 13 is a rear perspective view of the instrument drive assembly of FIG. 11.
Figure 14:
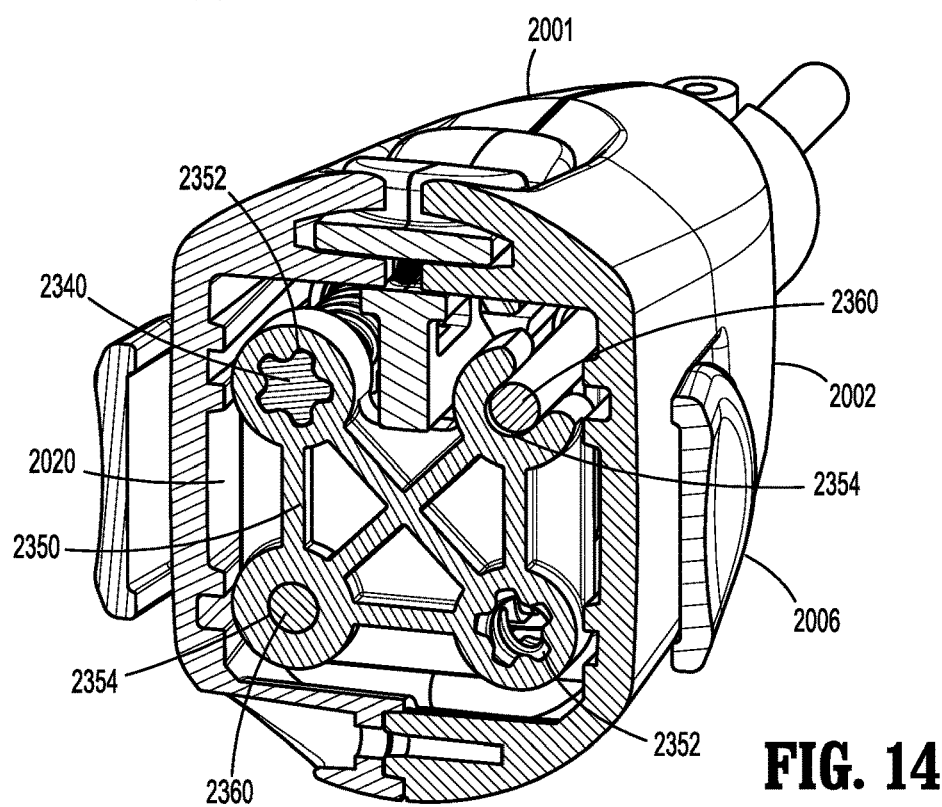
FIG. 14 is a perspective, cross-sectional view of the instrument drive assembly of FIG. 12 taken along the section line 14-14 of FIG. 13.
Figure 15:
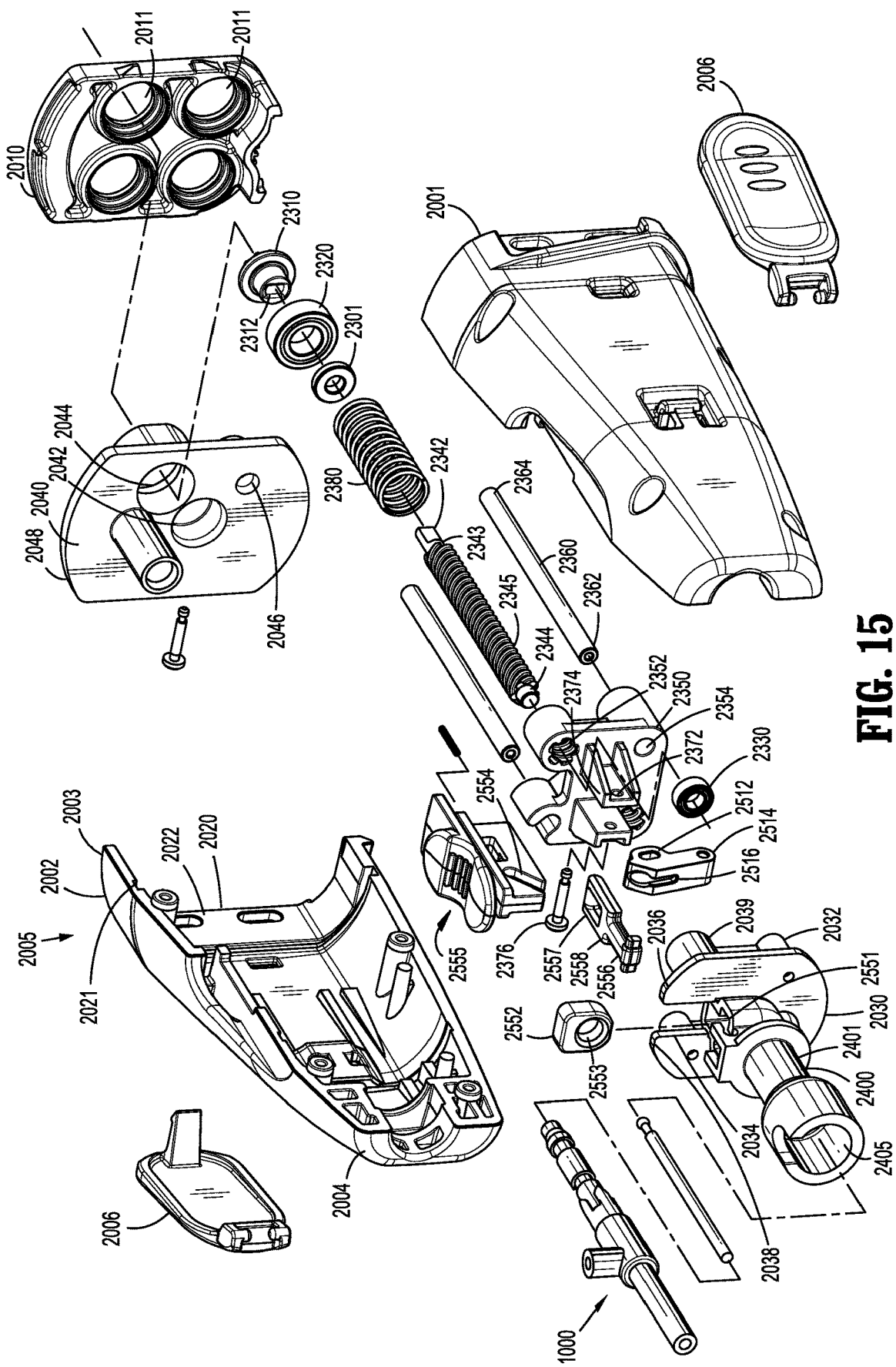
FIG. 15 is a parts separated view of the instrument drive assembly of FIG. 11.

With reference to FIGS. 11, 12 and 15, instrument drive assembly 2000 includes a housing assembly 2005 having a first side 2001 and a second side 2002, where first and second sides 2001, 2002 define a cavity 2020 therebetween. Housing assembly 2005 further includes a proximal end plate 2010 supported at a proximal end 2003 thereof, a distal end plate 2030 supported at a distal end 2004 thereof, a drive assembly 2300 supported in cavity 2020, an internal plate 2040 supported in cavity 2020, a coupling assembly 2500 disposed in cavity 2020, and a coupling tube 2400 supported by distal end plate 2030 and extending distally thereof. As best illustrated in FIG. 15, first and second sides 2001, 2002 of housing assembly 2005 act as two halves of a shell, with proximal end plate 2010 acting as a proximal wall and distal end plate 2030 acting as a distal wall. Housing assembly 2005 further includes a release mechanism 2006 disposed on first side 2001, second side 2002, and/or both first and second sides 2001, 2002. In a similar fashion as housing assembly 205 of instrument drive assembly 200, release mechanism 2006 of housing assembly 2005 serves to provide a quick and easy means for assembly or repair of internal components of instrument drive assembly 2000.

Proximal end plate 2010 of housing assembly 2005 defines at least one through-hole 2011 therein, and in an embodiment it is envisioned that proximal end plate 2010 may define four through-holes 2011 therein. Each through-hole 2011 is configured to receive a proximal gear 2310 of drive assembly 2300 therethrough, such that proximal gear 2310 may engage the instrument control gear of instrument control unit 100.

Figure 17:
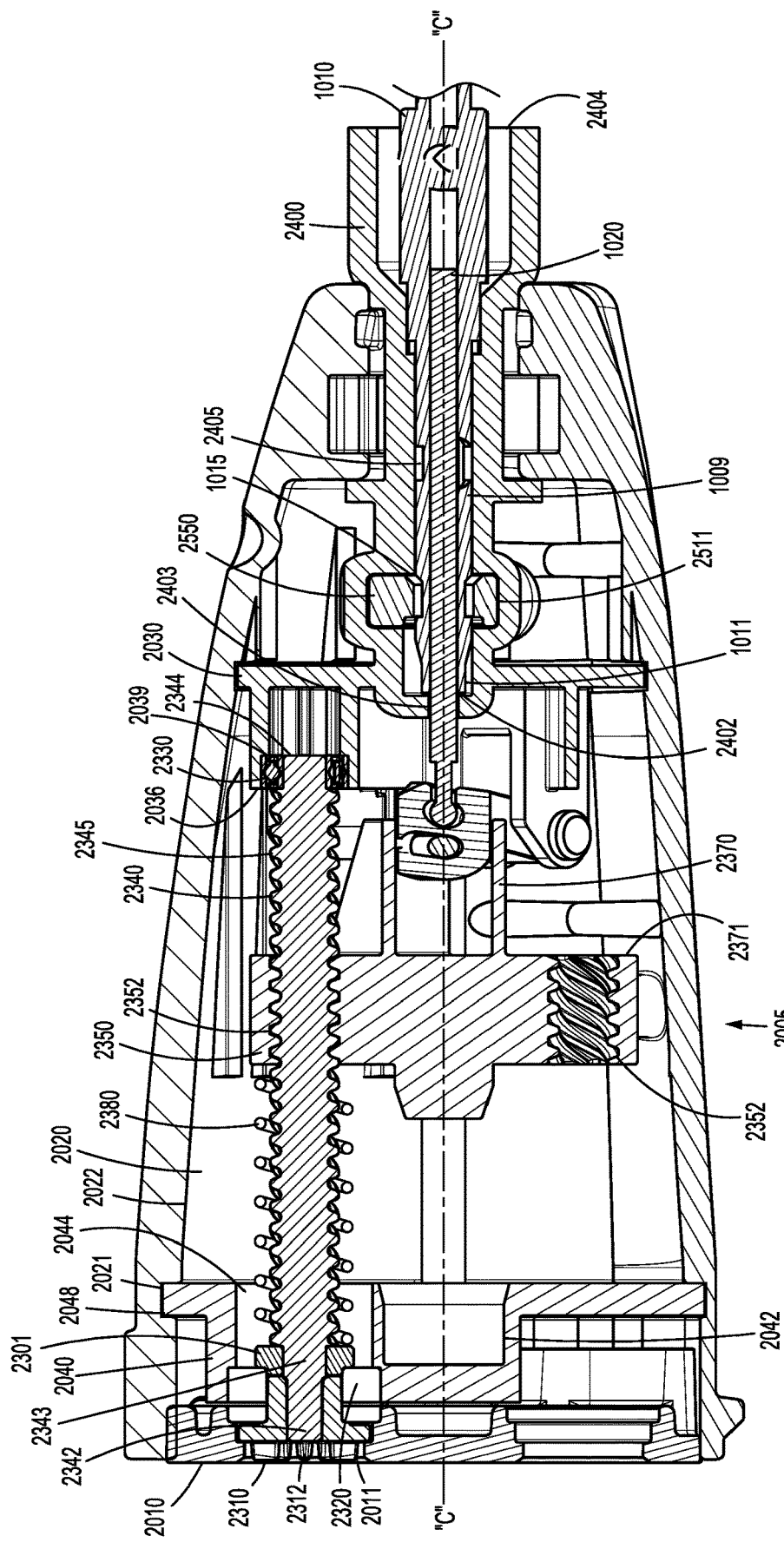
FIG. 17 is a side, cross-sectional view of the instrument drive assembly of FIG. 12 taken along the section line 17-17 of FIG. 13.

Distal end plate 2030 of housing assembly 2005 includes at least one rod receiving portion 2032 and at least one distal bearing cavity 2039, where the rod receiving portion 2032 and the distal bearing cavity 2039 are disposed on a proximal surface 2036 thereof. In an embodiment it is envisioned that distal end plate 2030 may include a pair of rod receiving portions 2032 laterally offset from each other. Distal end plate 2030 further defines an elongated cavity 2034, such that elongated cavity 2034 extends inward from an outer edge 2038 of distal end plate 2030 to align with a longitudinal axis "C" of housing assembly 2005 (FIGS. 11 and 17). It is envisioned that elongated cavity 2034 of distal end plate 2030 of housing assembly 2005 defines a generally "U" shaped cavity configured to support coupling tube 2400, such that coupling tube 2400 is supported therein and extends distally from cavity 2020 of housing assembly 2005, as described below.

Internal plate 2040 of housing assembly 2005 defines a first through-hole 2042 which is coaxial with the longitudinal axis "C" of housing assembly 2005, a second through-hole 2044 laterally offset from longitudinal axis "C" and which is coaxial with at least one through-hole 2011 of proximal end plate 2010, and at least one rod receiving portion 2046 laterally offset from longitudinal axis "C". A side edge 2048 of internal plate 2040 is supported in a channel 2021 defined in an inner surface 2022 of both first and second sides 2001, 2002 of housing assembly 2005, such that internal plate 2040 is fixed therein. It is envisioned that internal plate 2040 provides structural support for housing assembly 2005, and further provides support for drive assembly 2300, as discussed below.

Figure 16:
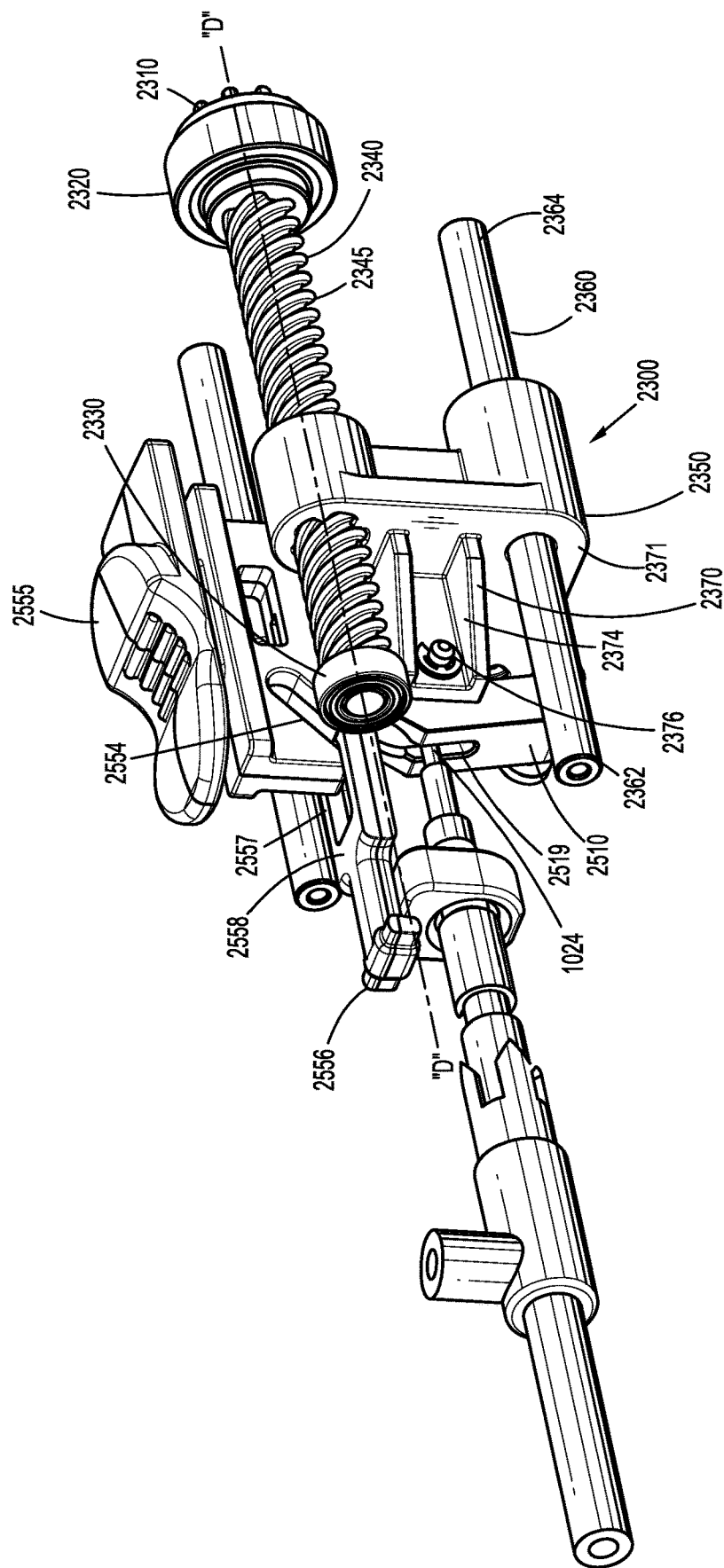
FIG. 16 is a front perspective view of the instrument drive assembly of FIG. 11 with various parts removed.

With reference to FIGS. 15-17, drive assembly 2300 of housing assembly 2005 will be further described. Drive assembly 2300 of housing assembly 2005 includes a proximal gear 2310, a proximal bearing 2320, a distal bearing 2330, a drive screw 2340, a drive plate 2350, and a guide rod 2360. Drive screw 2340 includes a proximal portion 2342, a proximal shaft 2343, a threaded portion 2345 and a distal shaft 2344, and defines a longitudinal axis "D" extending through a radial center thereof (FIG. 16). Proximal gear 2310 is configured to engage with the instrument control gear (e.g., crown gear "CG" of motor "M") of instrument control unit 100, such that rotation of crown gear "CG" causes a corresponding rotation of proximal gear 2310. Proximal gear 2310 may be a crown gear "CG" that is configured to mate with and/or mesh with crown gear "CG" of motor "M." Proximal gear 2310 includes an aperture 2312 extending longitudinally therethrough configured to mechanically engage proximal portion 2342 of drive screw 2340. As illustrated, aperture 2312 and proximal portion 2342 of drive screw 2340 have corresponding, non-circular cross-sections, such that proximal gear 2310 and drive screw 2340 are keyed to one another, which results in a rotationally fixed connection therebetween. Rotation of proximal gear 2310 causes drive screw 2340 to rotate about longitudinal axis "D" of drive screw 2340 in a corresponding direction and rate of rotation.

Drive plate 2350 of drive assembly 2300 includes at least one threaded aperture 2352 and at least one through-hole 2354 extending longitudinally therethrough. Threaded aperture 2352 is configured to mechanically engage threaded portion 2345 of drive screw 2340. That is, drive plate 2350 and drive screw 2340 of drive assembly 2300 are threadingly engaged with each other. Guide rod 2360 of drive assembly 2300 is slidably disposed in a through-hole 2354 of drive plate 2350, where a first end 2362 of guide rod 2360 is coupled to rod receiving portion 2032 of distal end plate 2030 and a second end 2364 of guide rod 2360 is coupled to rod receiving portion 2046 of internal plate 2040. It is envisioned that guide rod 2360 is laterally offset from, and parallel to, longitudinal axis "D" of drive screw 2340. It should be appreciated that housing assembly 2005 may include any number of guide rods 2360, where each guide rod 2360 is disposed in a respective rod receiving portion 2032 of proximal end plate 2030, a respective rod receiving portion 2046 of internal plate 2040, and a respective through-hole 2353 of drive plate 2350. In an embodiment, it is envisioned that housing assembly 2005 may include a pair of guide rods 2360, where guide rods 2360 are laterally offset from, and symmetrically spaced about, longitudinal axis "C" of housing assembly 2005. As such, guide rod 2360 inhibits or prevents drive plate 2350 from rotating about longitudinal axis "D" of drive screw 2340 as drive screw 2340 is rotated. Accordingly, drive plate 2350 is configured to be engaged with drive screw 2340 in a manner such that rotation of drive screw 2340 causes longitudinal translation of drive plate 2350. More specifically, rotation of proximal gear 2310 in a first direction (e.g., clockwise) causes drive screw 2340 to rotate in a corresponding first direction and drive plate 2350 to translate in a first longitudinal direction (e.g., proximally) with respect to proximal gear 2310, and rotation of proximal gear 2310 in a second direction (e.g., counter-clockwise) causes drive screw 2340 to rotate in a corresponding second direction and drive plate 2350 to translate in a second longitudinal direction (e.g., distally) with respect to proximal gear 2310.

Drive plate 2350 of drive assembly 2300 further includes a mounting bracket 2370 extending distally from a distal facing surface 2371 thereof. With brief reference to FIG. 15, mounting bracket 2370 of drive plate 2350 supports a coupling assembly 2500 thereon. Coupling assembly 2500 is configured to mechanically engage instrument drive shaft 1020 of surgical instrument 1000, such that proximal and distal translation of drive plate 2350, with respect to proximal gear 2310, results in proximal and distal translation of instrument drive shaft 1020, as discussed in further detail below. Longitudinal translation of drive plate 2350 is configured to drive a function of the end effector of surgical instrument 1000 in a similar fashion as drive member 380 of instrument drive assembly 200, and thus will not be discussed in any further detail herein. Longitudinal translation of drive plate 2350 further directs locking and unlocking of coupling assembly 2500 with respect to instrument drive shaft 1020, as discussed below.

With drive assembly 2300 and housing assembly 2005 assembled, proximal bearing 2320 of drive assembly 2300 is supported in through-hole 2011 of internal plate 2040, and distal bearing 2330 of drive assembly 2300 is disposed in distal bearing cavity 2039 of distal end plate 2030 (FIG. 17). Each of proximal bearing 2320 and distal bearing 2330 facilitate rotation of drive screw 2340 with respect to housing assembly 2005, where internal plate 2040 and distal end plate 2030 may serve as proximal and distal stops, respectively, for drive plate 2350. Drive assembly 2300 may further include a washer or spacer 2301 disposed about proximal shaft 2343 of drive screw 2030, between proximal bearing 2320 of drive assembly 2300 and threaded portion 2345 of drive screw 2340 of drive assembly 2300. Washer 2301 further facilitates rotation of drive screw 2340. Drive assembly 2300 may further include a biasing element 2380 disposed about drive screw 2340 between washer 2301 and drive plate 2350. Biasing element 2380 serves as a return spring providing distal bias to drive plate 2340, as discussed below.

Referring to FIG. 17, housing assembly 2005 further includes a coupling tube 2400. Coupling tube 2400 includes a proximal end 2402 defining a through-hole 2403, and a longitudinal bore or lumen 2405 extending distally therefrom. It is envisioned that longitudinal bore 2405 defines a larger diameter than through-hole 2403, such that longitudinal bore 2405 is configured to receive both instrument sleeve 1010 and instrument drive shaft 1020 of surgical instrument 1000 therein, and through-hole 2403 is configured to receive only instrument drive shaft 1020 therethrough, as discussed below. Coupling tube 2400 is supported in elongated cavity 2034 of distal end plate 2030 of housing assembly 2005 such that a distal portion 2401 of couple tube 2400 extends distally therefrom. It is envisioned that coupling tube 2400 may be monolithically formed with distal end plate 2030, or may alternatively be releasably couplable to elongated cavity 2034, such that coupling tube 2400 slides into and out of engagement with elongated cavity 2030. Longitudinal bore 2405 and through-hole 2403 of coupling tube 2400 define a longitudinal axis "T" of coupling tube 2400 (FIG. 18A), which may be coaxial with longitudinal axis "C" of housing assembly 2005. Longitudinal bore 2405 is configured to slidingly receive a proximal portion 1009 of instrument sleeve 1010. It is envisioned that during coupling of surgical instrument 1000 with instrument drive assembly 2000, coupling tube 2400 may aid alignment of instrument drive shaft 1020 and drive assembly 2300. More specifically, instrument sleeve 1010 of surgical instrument 1000 is slidably inserted into a distal opening 2404 of coupling tube 2400 of housing assembly 2005 of instrument drive assembly 2000. When instrument sleeve 1010 of surgical instrument 1000 is fully inserted into longitudinal bore 2405 of coupling tube 2400, a proximal end 1011 of instrument sleeve 1010 abuts a distally facing surface of proximal end 2402 of coupling tube 2400.

Housing assembly 2005 further includes a retention mechanism 2550 configured to releasably retain or secure instrument sleeve 1010 of surgical instrument 1000 to coupling tube 2400, and thus to housing assembly 2005. With reference to FIGS. 15, 16, and 18A-19D, retention mechanism 2550 includes a lock plate 2552, a button 2555, and a release arm 2558. Coupling tube 2400 of housing assembly 2005 defines a locking cavity 2551 disposed along a length thereof, such that lock plate 2552 is slidably insertable therein. Lock plate 2552 defines a through-hole 2553 configured to slidingly receive instrument sleeve 1010 therethrough, and is transitionable between a locked and unlocked configuration, with respect to instrument sleeve 1010, as discussed below. More specifically, in the locked configuration through-hole 2553 of lock plate 2552 is off-axis of, and offset or angled from, the longitudinal axis "T" of coupling tube 2400, and in the unlocked configuration through-hole 2553 of lock plate 2552 is coaxial with the longitudinal axis "T" of coupling tube 2400.

Release arm 2558 of retention mechanism 2550 defines an engagement region 2557 configured to engage a portion of button 2555, and an abutment region 2556, configured to abut lock plate 2552. Button 2555 is slidably coupled to housing assembly 2005, and actuatable between a first and second position. As button 2555 translates proximally, with respect to housing assembly 2005, button 2555 slides from the first position to the second position, such that the engagement region 2557 of release arm 2558 ride along a cam slot 2554 of button 2555. Cam slot 2554 of button 2555 has a first end 2554a and a second end 2554b, wherein when button 2555 is in the first position the engagement region 2557 of release arm 2558 is disposed at the first end 2554a of cam slot 2554 and the abutment region 2556 of release arm 2558 is spaced away from lock plate 2552. When button 2555 is in the second position the engagement region 2557 of release arm 2558 is disposed at the second end 2554b of cam slot 2554 and abutment region 2556 of release arm 2558 is in abutment with lock plate 2552. Accordingly, as engagement region 2557 cams along cam slot 2554, abutment region 2556 of release arm 2558 comes into and out of abutment with lock plate 2552, thus transitioning lock plate 2552 between the locked and unlocked configurations, respectively.

It is envisioned that the transition of button 2555 from the first position to the second position may correspond to the transitioning of lock plate 2552 into the unlocked configuration. It is contemplated that retention mechanism 2550 may further include a biasing member 2559 disposed in locking cavity 2551, such that lock plate 2552 is biased to the locked configuration. It is further contemplated that button 2555 includes a biasing member (not shown) supported thereon such that button 2555 is biased to the first position.

Figure 18C:
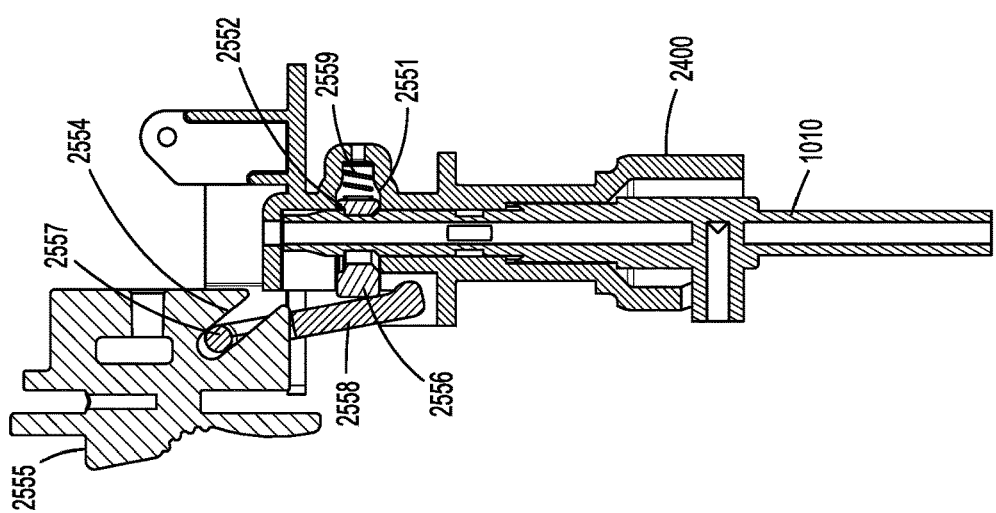

With continued reference to FIGS. 18A-19D, coupling and uncoupling of instrument sleeve 1010 of surgical instrument 1000 to coupling assembly 2500 of instrument drive assembly 2000 will be discussed. During coupling of instrument sleeve 1010 to coupling assembly 2500, instrument sleeve 1010 is inserted into distal opening 2404 of coupling tube and slid proximally therein (FIG. 18A). As the proximal end 1011 of instrument sleeve 1010 approaches the proximal end 2402 of coupling tube 2400, the proximal end 1011 of instrument sleeve 1010 urges lock plate 2551 to transition into the unlocked configuration (i.e., through-hole 2553 is coaxial with longitudinal axis "T" of coupling tube 2400) (FIG. 18B). As instrument sleeve 1010 continues to slide proximally, lock plate 2552 aligns with recess 1015 of instrument sleeve 1010, such that lock plate 2552 is permitted to transition into the locked configuration (i.e., through-hole 2553 is offset or angled from longitudinal axis "T" of coupling tube 2400) (FIG. 18C). With lock plate 2551 engaged within recess 1015 of instrument sleeve 1010, longitudinal translation of instrument sleeve 1010, within coupling tube 2400, is inhibited.

Figure 19B:
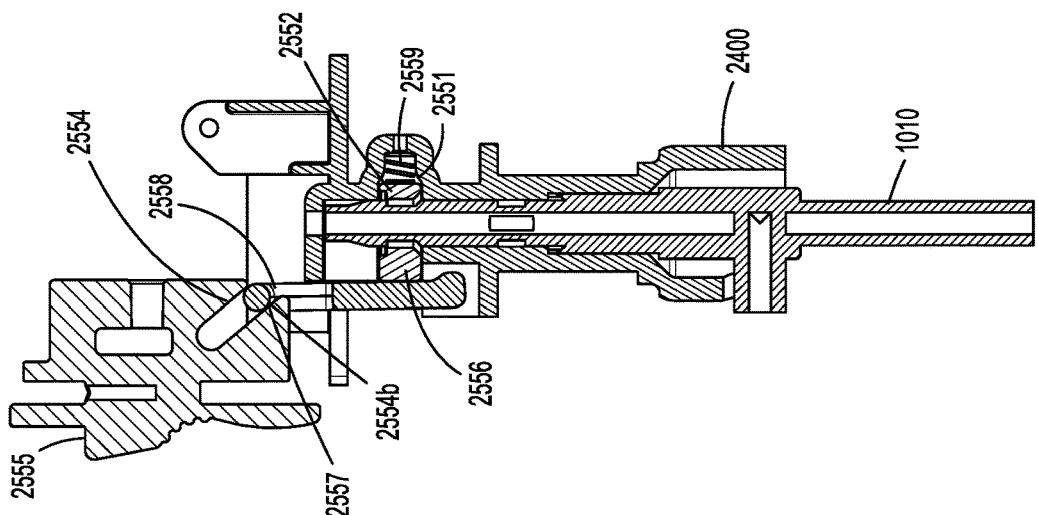
FIGS. 19A-19D are side views of the retention mechanism of FIGS. 18A-C in various states of actuation during removal of the instrument sleeve therefrom.
Figure 19A:
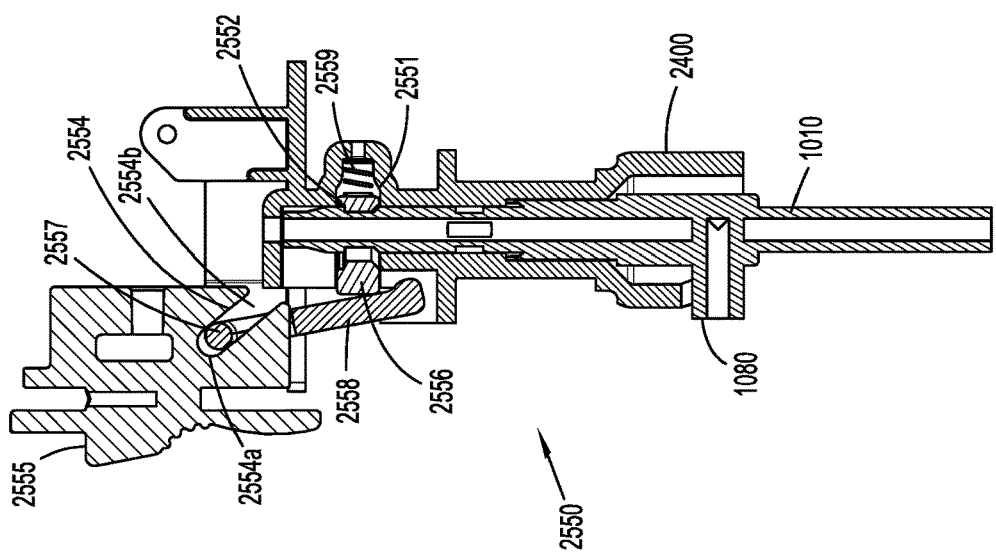
Figure 19C:
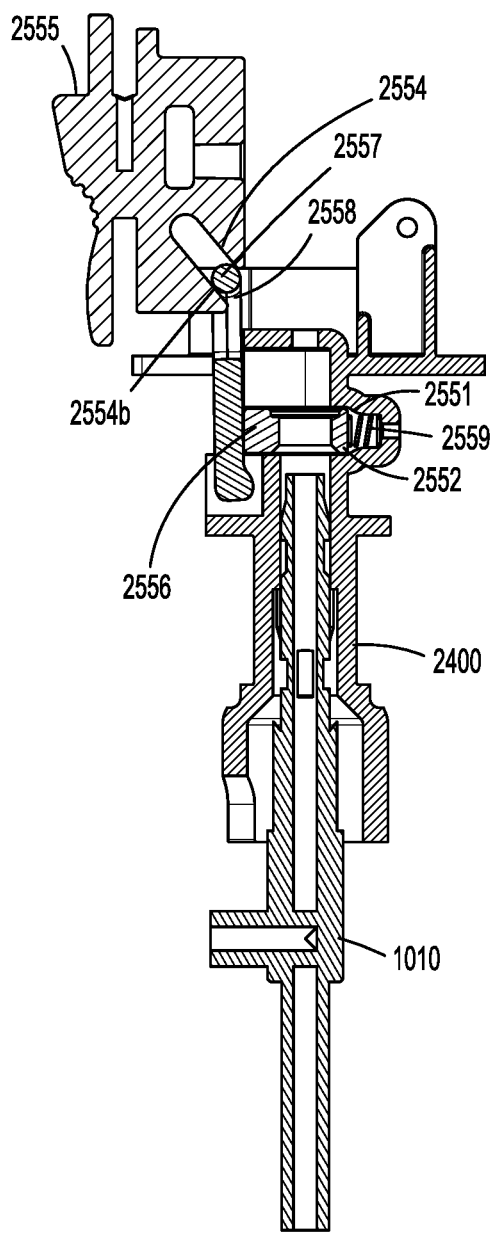
Figure 19D:
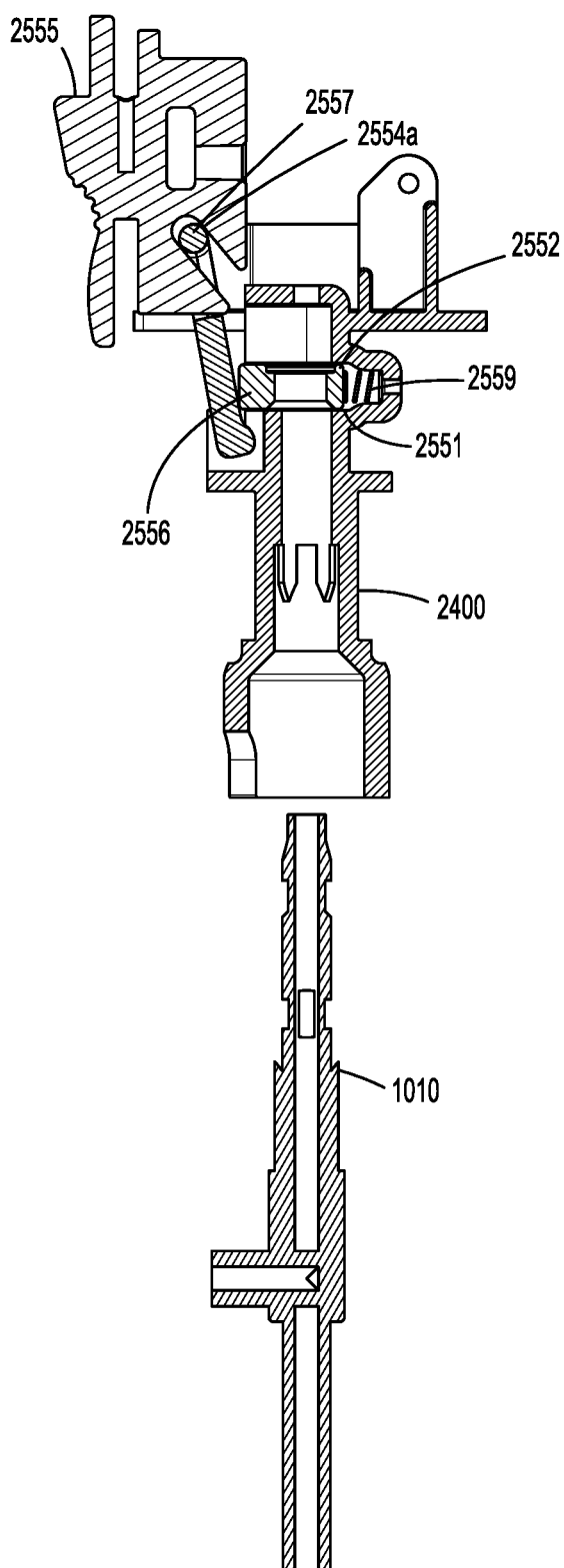

During uncoupling of instrument sleeve 1010 of surgical instrument 1000 from coupling assembly 2500 of instrument drive assembly 2000, button 2555 is transitioned into the second position, such that engagement region 2557 of release arm 2558 cams along cam slot 2554 of button 2555 into the second end 2554b of cam slot 2554 (FIGS. 19A and 19B). With engagement region 2557 at the second end 2554b of cam slot 2554, abutment region 2556 of release arm 2558 is brought into abutment with lock plate 2552, urging lock plate 2551 into the unlocked configuration (i.e., through-hole 2553 is coaxial with longitudinal axis "T" of coupling tube 2400) (FIG. 19B). With lock plate 2551 in the unlocked configuration, lock plate 2551 is disengaged from recess 1015 of instrument sleeve 1010, such that instrument sleeve 1010 is free to be withdrawn from and uncoupled from coupling tube 2400 (FIGS. 19C and 19D).

With reference to FIGS. 15 and 16, coupling assembly 2500 of instrument drive assembly 2000 will be discussed. Coupling assembly 2500 is disposed in cavity 2020 of housing assembly 2005 and supported by drive plate 2350. Coupling assembly 2500 serves to releasably couple instrument drive shaft 1020 of surgical instrument 1000 to drive assembly 2300 of housing assembly 2005. Coupling assembly 2500 engages with mounting bracket 2370 of drive plate 2350, which as noted above, extends distally from the distal facing surface 2371 of drive plate 2350.

Mounting bracket 2370 of drive plate 2350 is configured to pivotably support a drive link 2510 thereon, where drive link 2510 is configured to engage with, and couple to, instrument drive shaft 1020 of surgical instrument 1000, as discussed below. Mounting bracket 2370 includes a pair of receiving arms 2374, where receiving arms 2374 are spaced apart from one another and define a receiving nook or through-hole 2372 therein, where through-hole 2372 of each receiving arm 2374 is aligned such that a first pin 2376 may be disposed therein. Drive link 2510 is configured to be received between receiving arms 2374 of mounting bracket 2370, and is pivotably couple thereto via first pin 2376. First pin 2376 passed through each through-hole 2372 of receiving arms 2374 and a cam slot 2512 of drive link 2510. It is envisioned that drive link 2510 may alternatively be coupled to mounting bracket 2370 via a pair of extrusions or bosses extending from alternate sides of drive link 2510.

Drive link 2510 of coupling assembly 2500 further defines a through-hole 2514 therein, such that a second pin 2378 couples drive link 2510 to a through-hole 2407 disposed on a proximal portion 2408 of coupling tube 2400. It is envisioned that through-hole 2407 of coupling tube 2400 may be transverse to longitudinal axis "C" of housing assembly 2005. As such, when coupled, drive link 2510 is pivotably coupled to coupling tube 2400 between a locked position and an unlocked position, with respect to instrument drive shaft 1020 of surgical instrument 1000. More specifically, as drive plate 2350 of drive assembly 2300 translates proximally or distally, as discussed above, first pin 2376 rides along cam slot 2512 of drive link 2510 directing drive link 2510 to pivot about second pin 2378.

With reference to FIGS. 21A and 21B, drive link 2510 of coupling assembly 2500 further defines a receiving region 2516 disposed on a distal facing surface thereof, which is configured to releasably retain and secure coupling ball 1022 of instrument drive shaft 1020. Receiving region 2516 of drive link 2510 defines a cavity 2517 therein, a port 2518 extending into cavity 2517, and a channel 2519 extending along cavity 2517. Receiving region 2516 of drive link 2510 acts as a socket joint for coupling ball 1022 of instrument drive shaft 1020, where coupling ball 1022 can only enter and exit cavity 2517 through port 2518. Through pivoting of drive link 2510 between the unlocked and locked positions, port 2518 is correspondingly oriented to be aligned with, or brought off axis of, or angled from, longitudinal axis "T" of coupling tube 2400, respectively. More specifically, with drive link 2510 in the unlocked position, port 2518 is aligned with longitudinal axis "T", such that coupling ball 1022 of instrument drive shaft 1020 may be received therein. Once drive link 2510 is pivoted to the locked position, port 2518 is brought off-axis of, or angled from, longitudinal axis "T" of coupling tube 2400, and coupling ball 1022 of instrument drive shaft 1020 is captured within cavity 2517. In the locked position, neck 1024 of instrument shaft 1020 resides in channel 2519 of receiving region 2516 of drive link 2510, where channel 2519 is configured to be smaller than a diameter of coupling ball 1022, thus locking coupling ball 1022 in cavity 2517 of receiving region 2516 of drive link 2510. As such, port 2518 of receiving region 2516 of drive link 2510 is configured to receive coupling ball 1022 of instrument drive shaft 1020 therethrough, while channel 2519 of receiving region 216 of drive link 2510 is configured to inhibit coupling ball 1022 from leaving cavity 2517. With reference to FIGS. 21A and 21B, coupling ball 1022 (shown in phantom) is disposed in cavity 2517 of receiving region 2516 and neck 1024 is disposed in channel 2519.

Figure 20C:
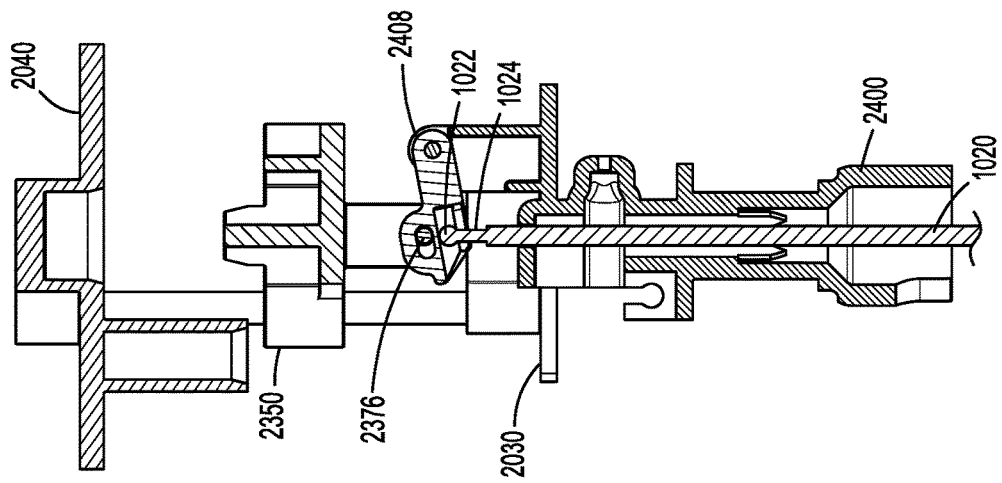
FIGS. 20A-20C are side views of a coupling assembly of the instrument drive assembly of FIG. 11 in various states of actuation during coupling of an instrument drive shaft therewith.
Figure 20B:
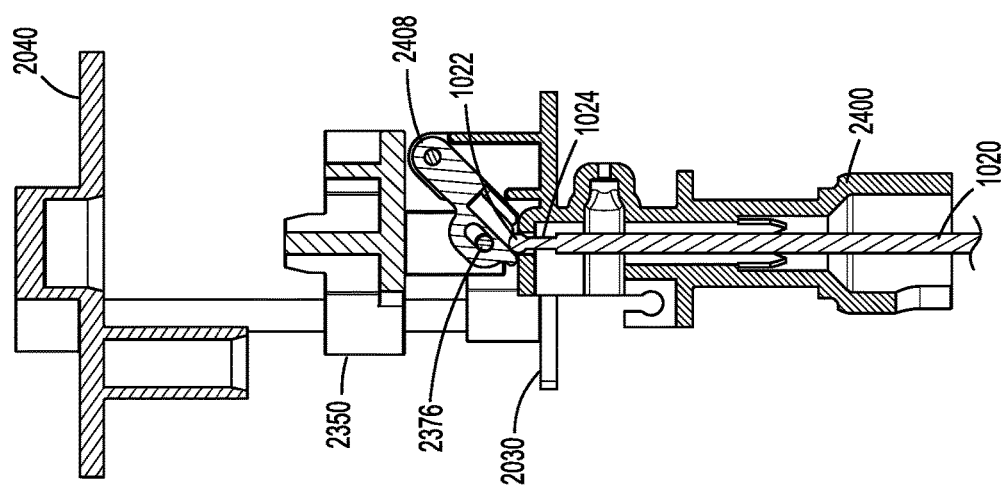
Figure 20A:
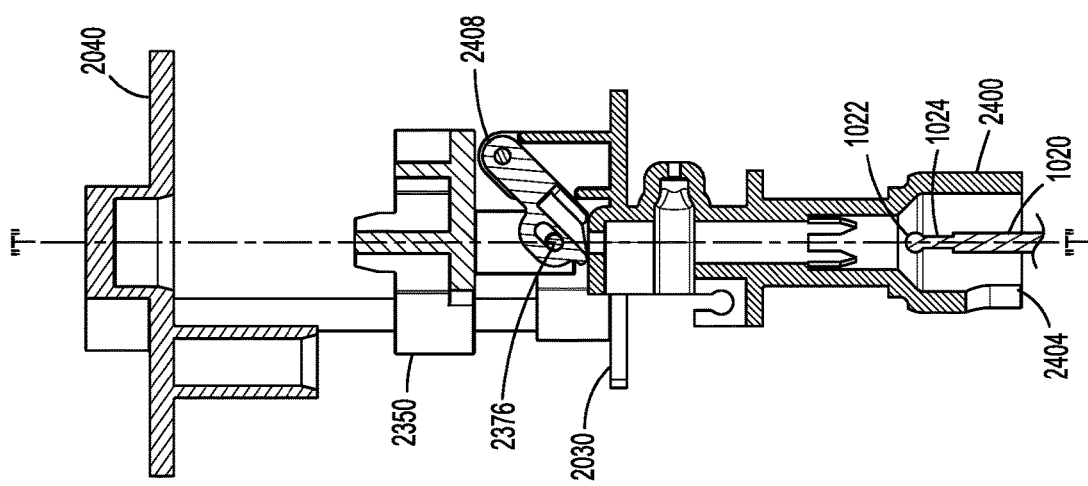

With reference to FIGS. 20A-20C, the engagement of instrument drive shaft 1020 of surgical instrument 1000 to coupling assembly 2500 of instrument drive assembly 2000 will be discussed. As discussed above, proximal and distal translation of drive plate 2350 of drive assembly 2300 pivots drive link 2510 between the unlocked position and the locked position, such that coupling assembly 2500 transitions between the unlocked and locked configuration, respectively. With drive plate 2350 in a distal most position, coupling assembly 2500 is in the unlocked configuration, drive link 2510 is in the unlocked position, such that port 2518 of drive link 2510 is aligned with longitudinal axis "T" of coupling tube 2400 (FIG. 20A). With port 2518 aligned with longitudinal axis "T", instrument drive shaft 1020 is inserted into the distal end 2404 of coupling tube 2400 and translated proximally, such that coupling ball 1022 of instrument drive shaft 1020 is brought into approximation with port 2518 of receiving region 2516 of drive link 2510. As instrument drive shaft 1020 translates proximally, coupling ball 1022 is inserted through port 2518 and brought into cavity 2517 of retention region 2516 of drive link 2510 (FIG. 20B). With coupling ball 1022 residing in cavity 2517, drive plate 2350 is translated proximally. As drive plate 2350 is translated proximally, first pin 2376 rides along cam slot 3512 of drive link 2510, such that drive link 2510 pivots about second pin 2378 into the locked position. With drive link 2510 in the locked position, neck 1024 of instrument shaft 1020 is disposed in channel 2519 of drive link 2510, thus capturing coupling ball 1022 within cavity 2517 of receiving region 2516 of drive link 2510 (FIG. 20C). Further, in the locked position, port 2518 of receiving region 2516 of drive link 2510 is brought off axis of, or angled from, the longitudinal axis "T" of coupling tube 2400. With drive link 2510 pivoted into the locked position, coupling assembly 2500 is thus in the locked configuration, with respect to instrument drive shaft 1020. Further proximal movement of drive plate 2350 causes drive link 2510 to pivot past the locked position directing proximal translation of instrument drive shaft 1020. Accordingly, proximal translation of drive plate 2350 causes drive plate 2510 to pivot past the locked position, thus directing proximal translation of instrument drive shaft 1020, which actuates the end effector (not shown) disposed at the distal end of instrument drive shaft 1020.

With reference to FIGS. 19A-20C, a complete coupling and decoupling of instrument drive assembly 2000 to surgical instrument 1000 will be briefly discussed. Initially, instrument sleeve 1010 of surgical instrument 1000 is inserted into coupling tube 2400 of housing assembly 2005 and translated proximally until lock plate 2552 of retention mechanism 2550 is brought into engagement with recess 1015 of instrument sleeve 1010, thus inhibiting any further translation of instrument sleeve 1010. It should be appreciated that coupling of instrument sleeve 1010 and retention mechanism 2550 may be performed with button 2555 of retention mechanism in either the first or second position. Next, drive plate 2350 of drive assembly 2300 is translated into a distal most position, such that drive link 2510 is pivoted into the unlocked position. Instrument drive shaft 1020 is then inserted proximally through instrument sleeve 1010 until coupling ball 1022 is engaged with drive link 2510. It is envisioned that instrument sleeve 1010 may alternatively be omitted, and thus instrument drive shaft 1020 may be inserted directly through coupling tube 2400. Once coupling ball 1022 is disposed in receiving region 2516 of drive link 2510, drive plate 2350 is translated proximally, such that drive link 2510 is pivoted into the locked position, and coupling assembly 2500 is translated into the locked configuration. Once instrument drive shaft 1020 is coupling with drive plate 2350, via drive link 2510, further proximal translation of drive plate 2350 directs actuation, articulation, or firing of the end effector of surgical instrument 1000.

During decoupling, drive plate 2350 of drive assembly 2300 is returned to the distal most position, such that drive link 2510 pivots to the unlocked position, and coupling assembly 2500 translates into the unlocked configuration. Instrument drive shaft 1020 of surgical instrument 1000 may now by translated distally, such that coupling ball 1022 is brought out of, or withdrawn from, receiving region 2516 of drive link 2510, and decoupled from instrument drive assembly 2000. Button 2555 of retention mechanism 2550 may then be translated into the second position, such that release arm 2558 abuts lock plate 2552, thus urging lock plate 2552 out of engagement with recess 1015 of instrument sleeve 1010 of surgical instrument 1000. Instrument sleeve 1010 may now be translated distally and withdrawn from coupling tube 2400. It is envisioned that outer sleeve 1010 and instrument drive shaft 1020 may be configured to be coupled, and uncoupled, independently and/or in any order.

During use of instrument drive assembly 2000, it should be appreciated that rotation of proximal gear 2310 of drive assembly 2300 in a first direction (e.g., clockwise) causes drive screw 2340 to rotate in a corresponding first direction, drive plate 2350 to translate in a first longitudinal direction (proximally), and drive link 2510 to pivot (towards the locked position as illustrated in FIG. 20C). Further translation of drive plate 2350 in the first longitudinal direction causes drive link 2510 to continue to pivot, past the locked position, such that instrument drive shaft 1020 is translated in the first longitudinal direction. Similarly, rotation of proximal gear 2310 of drive assembly 2300 in a second direction (e.g., counter-clockwise) causes drive screw 2340 to rotate in a corresponding second direction, drive plate 2350 to translate in a second longitudinal direction (distally), and drive link 2510 to pivot (towards the unlocked position as illustrated in FIG. 20B). As drive link 2510 pivots from a position past the locked position towards the locked position, instrument drive shaft 1020 is driven in the second longitudinal direction. Further translation of drive plate 2350 in the second longitudinal causes drive link 2510 to pivot into the unlocked position, such that instrument drive shaft 1020 may be decoupled therefrom.

It is contemplated that instrument sleeve 1010 of surgical instrument 1000 may further include a flush or inflation port 1080 disposed distally of proximal end 1011 (FIG. 11) of instrument sleeve 1010. Port 1080 may be used to introduce fluids into or out of the surgical site through longitudinal lumen 1012 of instrument sleeve 1010. Port 1080 may further be used as an alignment feature, such that at least one recess 900 disposed along distal opening 2404 of coupling tube 2400 acts as a keying feature for instrument sleeve 1010 and/or instrument drive shaft 1020 (FIG. 12) of surgical instrument 1000. It is envisioned that at least two recesses 900 may be included and spaced 180° apart about distal opening 2404 of coupling tube 2400. It is envisioned that coupling tube 400 of instrument drive assembly 200 may similarly define a recess disposed along distal opening 404 to serve as a keying feature when coupling instrument drive assembly 200 and instrument sleeve 1010 of surgical instrument 1000.

With reference to FIGS. 1-21B, a kit will be described. A kit may include one or more instrument drive assemblies 200, one or more instrument drive assemblies 2000, or any combination thereof. The kit may further include one or more surgical instruments 1000, where the end effector of each surgical instrument varies to provide a number of end effector options to a user. It is further envisioned that the kit may include alternate instrument sleeves 1010 and/or instrument drive shafts 1020, such that the operator may interchange instrument sleeves 1010 and instrument drive shafts 1020 for a given procedure. A variety of instrument sleeves 1010 and/or instrument drive shafts 1020 defining a range of lengths and/or diameters, respectively, may be provided to the user, such that the user has a variety of sized surgical instrument 1000 available.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. An instrument drive assembly for use with a surgical instrument, the instrument drive assembly comprising:
 a coupling tube;
 a coupling assembly supported on the coupling tube, the coupling assembly configured to releasably couple to an instrument drive shaft of the surgical instrument;
 a retention mechanism configured to releasably couple to an instrument sleeve of the surgical instrument;
 a drive screw defining a threaded portion;
 a drive nut threadingly engaged with the threaded portion of the drive screw such that rotation of the drive screw results in longitudinal movement of the drive nut along a longitudinal axis of the drive screw; and
 a drive member coupled to the drive nut and extending distally therefrom, wherein longitudinal translation of the drive member drives a function of the surgical instrument.

2. The instrument drive assembly of claim 1, wherein the coupling assembly is slidably supported on the coupling tube and the coupling tube interconnects a housing assembly of the instrument drive assembly and the coupling assembly, such that a portion of the drive member of the drive assembly is disposed within the coupling tube.

3. The instrument drive assembly of claim 2, wherein the retention mechanism is disposed within the coupling assembly.

4. The instrument drive assembly of claim 3, wherein the retention mechanism is biased into one of a locked configuration or an unlocked configuration with respect to the instrument sleeve of the surgical instrument.

5. The instrument drive assembly of claim 4, wherein in the locked configuration the retention mechanism is positioned on a longitudinal axis of the coupling tube, and in the unlocked configuration the retention mechanism is positioned radially away from the longitudinal axis of the coupling tube, such that the retention mechanism comes into and out of abutment with the instrument sleeve.

6. The instrument drive assembly of claim 5, wherein the coupling assembly is slidable along the coupling tube between a distal position and a proximal position with respect to the housing assembly, and wherein the retention mechanism is in the locked configuration when the coupling assembly is in the distal position, and the retention mechanism is in the unlocked configuration when the coupling assembly is in the proximal position.

7. The instrument drive assembly of claim 6, wherein the coupling assembly is biased into one of the proximal or distal positions.

8. The instrument drive assembly of claim 3, wherein the drive member further includes an engagement region disposed at a distal end thereof, the engagement region configured to releasably couple with a proximal end of the instrument drive shaft of the surgical instrument.

9. The instrument drive assembly of claim 8, wherein the engagement region of the drive member defines an expandable leafed socket being flexible radially outward, and the instrument drive shaft defines a coupling ball disposed at a proximal end thereof, wherein the socket flexes radially outward to facilitate coupling and uncoupling of the coupling ball of the instrument drive shaft to the engagement region of the drive member.

10. The instrument drive assembly of claim 9, wherein the socket of the engagement region further includes a plurality of retention hooks disposed at a distal end thereof and on an inner facing surface thereof, the retention hooks configured to facilitate retention of the coupling ball of the instrument drive shaft within the socket of the engagement region.

11. An instrument drive assembly for use with a surgical instrument, the instrument drive assembly comprising:
   a coupling tube;
   a coupling assembly supported on the coupling tube, the coupling assembly configured to releasably couple to an instrument drive shaft of the surgical instrument;
   a retention mechanism configured to releasably couple to an instrument sleeve of the surgical instrument;
   a drive screw defining a threaded portion; and
   a drive plate threadingly engaged with the threaded portion of the drive screw such that rotation of the drive screw results in longitudinal movement of the drive plate along a longitudinal axis of the drive screw.

12. The instrument drive assembly of claim 11, wherein the retention mechanism is supported in a housing assembly and includes:
   a lock plate transitionable between a locked configuration and unlocked configuration with respect to the instrument sleeve of the surgical instrument;
   a button slidable between a first position and a second position; and
   a release arm defining an engagement region configured to engage the button, and an abutment region configured to abut the lock plate,
   wherein in the first position of the button the abutment region of the release arm is spaced away from the lock plate and the lock plate is in the locked position, and in the second position of the button the abutment region of the release arm is in abutment with the lock plate and the lock plate is in the unlocked configuration.

13. The instrument drive assembly of claim 12, wherein the button defines a cam slot including a first end and a second end, the engagement region of the release arm translatable along the cam slot of the button between the first and second ends of the cam slot such that with the engagement region at the first end of the cam slot, the button is in the first position, and the lock plate is in the locked configuration, and with the engagement region at the second end of the cam slot, the button is in the second position, and the lock plate is in the unlocked configuration.

14. The instrument drive assembly of claim 12, wherein the lock plate defines a through-hole configured to receive the instrument sleeve therein, such that in the locked configuration of the lock plate an inner surface of the through-hole abuts an outer surface of the instrument sleeve and in the unlocked configuration the inner surface of the through-hole is spaced away from the outer surface of the instrument sleeve.

15. The instrument drive assembly of claim 11, wherein the coupling assembly includes a drive link pivotably coupled to a distal portion of the coupling tube and fixedly coupled to a distally facing surface of the drive plate of the drive assembly.

16. The instrument drive assembly of claim 15, wherein the drive link includes a cam slot at a first end and through-hole at a second end thereof, such that a cam pin couples the drive link to the drive plate through the cam slot of the drive link, and a pin couples the drive link to the distal portion of the coupling tube through the through-hole of the drive link.

17. The instrument drive assembly of claim 16, wherein proximal and distal translation of the drive plate of the drive assembly drives the cam pin within the cam slot of the drive plate, such that the proximal and distal translation of the drive plate pivots the drive link about the pin and through-hole between a locked position and an unlocked position.

18. The instrument drive assembly of claim 17, wherein the drive link further includes a receiving region disposed on a distally facing surface thereof, the receiving region including:
   a cavity defined therein, the cavity configured to receive a coupling ball disposed at a proximal end of the instrument drive shaft therein;
   a port extending into the cavity, the port configured to receive the coupling ball of the instrument drive shaft therethrough; and
   a channel extending along the cavity, the channel configured to receive a portion of the instrument drive shaft distal of the coupling ball therein,
   wherein the receiving region of the drive link is configured to releasably couple the coupling ball of the instrument drive shaft to the drive plate.

19. The instrument drive assembly of claim 18, wherein in the unlocked position of the drive link the drive plate of the drive assembly is in a distal most position such that the port of the receiving region of the drive link is coaxial with a longitudinal axis of the coupling tube, and wherein in the locked position of the drive link the drive plate of the drive assembly is in a position proximal of the distal most position such that the port of the receiving region is angled from the longitudinal axis of the coupling tube.

20. The instrument drive assembly of claim 19, wherein in the locked position the coupling ball of the instrument drive shaft is retained within the cavity of the receiving region and the portion of the instrument drive shaft distal of the coupling ball resides within the channel of the receiving region.

21. An instrument drive assembly for use with a surgical instrument, the instrument drive assembly comprising:
   a coupling tube;
   a coupling assembly supported on the coupling tube, the coupling assembly configured to releasably couple to an instrument drive shaft of the surgical instrument;
   a retention mechanism configured to releasably couple to an instrument sleeve of the surgical instrument;
   a drive screw defining a threaded portion;
   a drive nut threadingly engaged with the threaded portion of the drive screw such that longitudinal movement of the drive nut along a longitudinal axis of the drive screw results in rotation of the drive screw; and
   a drive member coupled to the drive nut and extending distally therefrom, wherein longitudinal translation of the drive member drives a function of the surgical instrument.

* * * * *